United States Patent
Maxwell et al.

(10) Patent No.: US 7,927,872 B2
(45) Date of Patent: Apr. 19, 2011

(54) ALDOS AS MODIFIERS OF THE IGF PATHWAY AND METHODS OF USE

(75) Inventors: Mark E. Maxwell, Lansdale, PA (US); Michael Martin Ollmann, Redwood City, CA (US); Timothy S. Heuer, El Granada, CA (US); Benjamin C. Hitz, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 383 days.

(21) Appl. No.: 11/628,487

(22) PCT Filed: Jun. 20, 2005

(86) PCT No.: PCT/US2005/021653
§ 371 (c)(1),
(2), (4) Date: Sep. 14, 2008

(87) PCT Pub. No.: WO2006/009950
PCT Pub. Date: Jan. 26, 2006

(65) Prior Publication Data
US 2009/0022737 A1    Jan. 22, 2009

Related U.S. Application Data

(60) Provisional application No. 60/581,689, filed on Jun. 21, 2004.

(51) Int. Cl.
*C12N 5/00* (2006.01)
*C12Q 1/42* (2006.01)
(52) U.S. Cl. .............. 435/375; 435/21; 435/6; 435/7; 435/18; 435/7.1; 536/23.2
(58) Field of Classification Search ............... 435/375, 435/18, 6, 7.21, 7.1; 536/23.2
See application file for complete search history.

(56) References Cited

U.S. PATENT DOCUMENTS 7,414,119 B2 * 8/2008 Greenberg et al. ......... 536/23.2
2004/0248142 A1 12/2004 Kinoshita et al.

FOREIGN PATENT DOCUMENTS

| JP | 2004 105013 A | 4/2004 |
| WO | WO 02/077176 A | 10/2002 |
| WO | WO 03/010336 A | 2/2003 |
| WO | WO 03/100008 A | 12/2003 |

OTHER PUBLICATIONS

Song H. et al.: "Genes encoding Pir51, Beclin 1, RbAp48 and aldolase b are up or down-regulated in human primary hepatocellular carcinoma," World Journal of Gastroenterology, vol. 10, No. 4, Feb. 15, 2004, pp. 509-513.
Gure et al.: "Human lung cancer antigens recognized by autologous antibodies: definition of a novel cDNA derived from the tumor suppressor gene locus on chromosome 3p21.3." Cancer research, American Association for Cancer Research, Baltimore, MD, US, vol. 58, Mar. 1, 1998, pp. 1034-1041.
Patrick H. Maxwell et al.: "Activation of the HIF pathway in cancer," Current Opinion in Genetics and Development, vol. 11, No. 3, Jun. 2001, pp. 293-299.
Moorehead, et al., "Transgenic overexpression of IGF-II induces spontaneous lung tumors: a model for human lung adenocarcinoma.", Oncogene, 2003, vol. 22, pp. 583-587.

* cited by examiner

*Primary Examiner* — Tekchand Saidha
(74) *Attorney, Agent, or Firm* — McDonnell Boehnen Hulbert & Berghoff LLP

(57) ABSTRACT

Human ALDO genes are identified as modulators of the IGF pathway, and thus are therapeutic targets for disorders associated with defective IGF function. Methods for identifying modulators of IGF, comprising screening for agents that modulate the activity of ALDO are provided.

15 Claims, No Drawings

ALDOS AS MODIFIERS OF THE IGF PATHWAY AND METHODS OF USE

REFERENCE TO RELATED APPLICATIONS

This application claims priority to U.S. provisional patent application 60/581,689 filed Jun. 21, 2004. The contents of the prior application are hereby incorporated in their entirety.

BACKGROUND OF THE INVENTION

Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN is thought to act as a tumor suppressor by regulating several signaling pathways through the second messenger phosphatidylinositol 3,4,5 triphosphate (PIP3). PTEN dephosphorylates the D3 position of PIP3 and downregulates signaling events dependent on PIP3 levels (Maehama T and Dixon J E (1998) J Biol Chem, 22, 13375-8). In particular, pro-survival pathways downstream of the insulin-like growth factor (IGF) pathway are regulated by PTEN activity. Stimulation of the IGF pathway, or loss of PTEN function, elevates PIP3 levels and activates pro-survival pathways associated with tumorigenesis (Stambolic V et al. (1998) Cell, 95:29-39). Consistent with this model, elevated levels of insulin-like growth factors I and II correlate with increased risk of cancer (Yu H et al (1999) J Natl Cancer Inst 91:151-156) and poor prognosis (Takanami I et al, 1996, J Surg Oncol 61(3):205-8).

PTEN sequence is conserved in evolution, and exists in mouse (Hansen GM and Justice M J (1998) Mamm Genome, 9(1):88-90), Drosophila (Goberdhan D C et al (1999) Genes and Dev, 24:3244-58; Huang H et al (1999) Development 23:5365-72), and C. elegans (Ogg S and Ruvkun G, (1998) Mol Cell, (6):887-93). Studies in these model organisms have helped to elucidate the role of PTEN in processes relevant to tumorigenesis. In Drosophila, the PTEN homolog (dPTEN) has been shown to regulate cell size, survival, and proliferation (Huang et al, supra; Goberdhan et al, supra; Gao X et al, 2000, 221:404-418). In mice, loss of PTEN function increases cancer susceptibility (Di Cristofano A et al (1998) Nature Genetics, 19:348-355; Suzuki A et al (1998) Curr. Biol., 8:1169-78).

In addition, a member of the IGF/insulin receptor family exists in Drosophila and has been shown to respond to insulin stimulation (Fernandez-Almonacid R, and Rozen O M (1987) Mol Cell Bio, (8):2718-27). Similar to PTEN, studies in Drosophila (Brogiolo W et al (2001) Curr Biol, 11(4):213-21) and mouse (Moorehead R A et al (2003) Oncogene, 22(6):853-857) establish a conserved role for the IGF/insulin pathway in growth control.

Fructose-1,6-bisphosphate aldolase (ALDO) is a glycolytic enzyme that catalyzes the reversible conversion of fructose-1,6-bisphosphate to glyceraldehyde 3-phosphate and dihydroxyacetone phosphate. The enzyme is a tetramer of identical 40,000-dalton subunits. Vertebrates have 3 aldolase isozymes which are distinguished by their electrophoretic and catalytic properties. The amino acid sequence of the aldolases around the active site lysine is greatly conserved in evolution. Differences indicate that aldolases A (ALDOA), B (ALDOB), and C (ALDOC) are distinct proteins, the products of a family of related genes. Study of the genes is of interest because expression of the isozymes is regulated during development and because they represent the poorly characterized class of 'housekeeping genes' which are expressed in all cells. The developing embryo produces ALDOA, which is produced in even greater amounts in adult muscle where it can be as much as 5% of total cellular protein. In adult liver, kidney and intestine, ALDOA expression is repressed and ALDOB is produced. In brain and other nervous tissue, ALDOA and ALDOC are expressed about equally. In transformed liver cells, ALDOA replaces ALDOB.

The ability to manipulate the genomes of model organisms such as Drosophila provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism or cell having underexpression (e.g. knockout) or overexpression of a gene (referred to as a "genetic entry point") that yields a visible phenotype, such as altered cell growth. Additional genes are mutated in a random or targeted manner. When a gene mutation changes the original phenotype caused by the mutation in the genetic entry point, the gene is identified as a "modifier" involved in the same or overlapping pathway as the genetic entry point. When inactivation of either gene is not lethal, but inactivation of both genes results in reduced viability or death of the cell, tissue, or organism, the interaction is defined as "synthetic lethal" (Bender, A and Pringle J, (1991) Mol Cell Biol, 11:1295-1305; Hartman J et al, (2001) Science 291:1001-1004; U.S. Pat. No. 6,489,127). In a synthetic lethal interaction, the modifier may also be identified as an "interactor". When the genetic entry point is an ortholog of a human gene implicated in a disease pathway, such as the IGF pathway, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the IGF pathway in Drosophila cells, and identified their human orthologs, hereinafter referred to as Fructose-1,6-bisphosphate aldolase (ALDO). The invention provides methods for utilizing these IGF modifier genes and polypeptides to identify ALDO-modulating agents that are candidate therapeutic agents that can be used in the treatment of disorders associated with defective or impaired IGF function and/or ALDO function. Preferred ALDO-modulating agents specifically bind to ALDO polypeptides and restore IGF function. Other preferred ALDO-modulating agents are nucleic acid modulators such as antisense oligomers and RNAi that repress ALDO gene expression or product activity by, for example, binding to and inhibiting the respective nucleic acid (i.e. DNA or mRNA).

ALDO modulating agents may be evaluated by any convenient in vitro or in vivo assay for molecular interaction with an ALDO polypeptide or nucleic acid. In one embodiment, candidate ALDO modulating agents are tested with an assay system comprising an ALDO polypeptide or nucleic acid. Agents that produce a change in the activity of the assay system relative to controls are identified as candidate IGF modulating agents. The assay system may be cell-based or cell-free. ALDO-modulating agents include ALDO related proteins (e.g. dominant negative mutants, and biotherapeutics); ALDO-specific antibodies; ALDO-specific antisense oligomers and other nucleic acid modulators; and chemical agents that specifically bind to or interact with ALDO or compete with ALDO binding partner (e.g. by binding to an ALDO binding partner). In one specific embodiment, a small molecule modulator is identified using an aldolase assay. In specific embodiments, the screening assay system is selected from a binding assay, an apoptosis assay, a cell proliferation assay, an angiogenesis assay, and a hypoxic induction assay.

In another embodiment, candidate IGF pathway modulating agents are further tested using a second assay system that detects changes in the IGF pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the IGF pathway, such as an angiogenic, apoptotic, or cell proliferation disorder (e.g. cancer).

The invention further provides methods for modulating the ALDO function and/or the IGF pathway in a mammalian cell by contacting the mammalian cell with an agent that specifically binds an ALDO polypeptide or nucleic acid. The agent may be a small molecule modulator, a nucleic acid modulator, or an antibody and may be administered to a mammalian animal predetermined to have a pathology associated with the IGF pathway.

DETAILED DESCRIPTION OF THE INVENTION

The PTEN co-RNAi plus insulin synthetic interaction screen was designed to identify modifier genes that are lethal or reduce proliferation in cells with a hyperstimulated IGF/insulin pathway, but not in normal cells. We refer to these genes as "synthetic lethal" genes in the context of this screen. To identify these genes, we created cells with a hyperstimulated IGF/insulin pathway by treatment with insulin and RNAi-mediated inactivation of dPTEN, the Drosophila homologue of the human tumor suppressor PTEN. In addition to identifying genes with synthetic lethal interactions in insulin-treated, PTEN-deficient cells, this screen identified genes that, when inactivated, preferentially suppressed multiple readouts known to be regulated by IGF signaling. For our screen, these readouts included an expression assay for a IGF/insulin reporter gene and quantitative Western blot readouts for several nodes in the IGF/insulin pathway (phospho-4E-BP, phospho-MAPK, phospho-S6K, and total RpS6).

In a preferred embodiment, the Drosophila IGF modifier screen identified genes that, when inactivated, preferentially suppressed insulin-induced Lactate Dehydrogenase (LDH) expression and hence may be key mediators of IGF/PTEN signaling. Lactate Dehydrogenase (LDH) is a well-validated target of the Drosophila Insulin/IGF pathway. We confirmed this finding by analyzing gene expression in insulin-stimulated Drosophila S2 cells by microarray expression analysis (Affymetrix), which showed significant increases in expression of the LDH gene. This result was confirmed by Quantitative PCR (TAQMAN®) assay that detected a 12-fold increase in LDH expression in cells treated with either 1 µM insulin or dsRNA specific to the dPTEN gene. The use of LDH as a reporter gene has also been validated by RNAi of known positive mediators of IGF signaling such as InR, IRS, Tor, and Rheb, which results in substantially decreased LDH expression in the assay. In contrast, RNAi of known negative regulators of IGF signaling (TSC1 and TSC2) results in an increase in LDH expression. To further confirm that modifiers that decrease insulin-induced expression of LDH have relevance to IGF/PTEN signaling, we performed Quantitative Western Blots to determine whether RNAi of each modifier decreased phosphorylation of 4E-BP (a downstream gene that is phosphorylated by the Tor kinase) or affected S6K (Thr389) phosphorylation, MAPK phosphorylation, or total RPS6 protein levels. The DROSOPHILA ALD gene was identified as a modifier of the IGF pathway. Accordingly, vertebrate orthologs of this modifier, and preferably the human orthologs, ALDO genes (i.e., nucleic acids and polypeptides) are attractive drug targets for the treatment of pathologies associated with a defective IGF signaling pathway, such as cancer.

In vitro and in vivo methods of assessing ALDO function are provided herein. Modulation of the ALDO or their respective binding partners is useful for understanding the association of the IGF pathway and its members in normal and disease conditions and for developing diagnostics and therapeutic modalities for IGF related pathologies. ALDO-modulating agents that act by inhibiting or enhancing ALDO expression, directly or indirectly, for example, by affecting an ALDO function such as enzymatic (e.g., catalytic) or binding activity, can be identified using methods provided herein. ALDO modulating agents are useful in diagnosis, therapy and pharmaceutical development.

Nucleic Acids and Polypeptides of the Invention

Sequences related to ALDO nucleic acids and polypeptides that can be used in the invention are disclosed in Genbank (referenced by Genbank identifier (GI) number) as GI#s 34577108 (SEQ ID NO:1), 28594 (SEQ ID NO:2), 28613 (SEQ ID NO:3), 49456714 (SEQ ID NO:4), 50471500 (SEQ ID NO:5), 40354204 (SEQ ID NO:6), 178355 (SEQ ID NO:7), 10439268 (SEQ ID NO:8), 20809494 (SEQ ID NO:9), 4885062 (SEQ ID NO: 10), 28598 (SEQ ID NO: 11), and 28600 (SEQ ID NO: 12), for nucleic acid, and GI#s 4557305 (SEQ ID NO: 13), 40354205 (SEQ ID NO: 14), and 4885063 (SEQ ID NO: 15) for polypeptide sequences.

The term "ALDO polypeptide" refers to a full-length ALDO protein or a functionally active fragment or derivative thereof. A "functionally active" ALDO fragment or derivative exhibits one or more functional activities associated with a full-length, wild-type ALDO protein, such as antigenic or immunogenic activity, enzymatic activity, ability to bind natural cellular substrates, etc. The functional activity of ALDO proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active ALDO polypeptide is an ALDO derivative capable of rescuing defective endogenous ALDO activity, such as in cell based or, animal assays; the rescuing derivative may be from the same or a different species. For purposes herein, functionally active fragments also include those fragments that comprise one or more structural domains of an ALDO, such as an aldolase domain or a binding domain. Protein domains can be identified using the PFAM program (Bateman A., et al., Nucleic Acids Res, 1999, 27:260-2). For example, the Fructose-bisphosphate aldolase domain (PFAM 00274) of ALDO from GI#s 4557305, 40354205, and 4885063 (SEQ ID NOs:13, 14, and 15, respectively) is located respectively at approximately amino acid residues 15-364, 15-364, and 15-364. Methods for obtaining ALDO polypeptides are also further described below. In some embodiments, preferred figments are functionally active, domain-containing fragments comprising at least 25 contiguous amino acids, preferably at least 50, more preferably 75, and most preferably at least 100 contiguous amino acids of an ALDO. In further preferred embodiments, the fragment comprises the entire functionally active domain.

The term "ALDO nucleic acid" refers to a DNA or RNA molecule that encodes an ALDO polypeptide. Preferably, the ALDO polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human ALDO. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows specification, a single gene in one species, such as Drosophila, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of an ALDO. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of an ALDO under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% FICOLL®, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of ALDO Nucleic Acids and Polypeptides ALDO nucleic acids and polypeptides are useful for identifying and testing agents that modulate ALDO function and for other applications related to the involvement of ALDO in the IGF pathway. ALDO nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an ALDO protein for assays used to assess ALDO function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant ALDO is expressed in a cell line known to have defective IGF function. The recombinant cells are used in cell-based screening assay systems of the invention, as described further below.

The nucleotide sequence encoding an ALDO polypeptide can be inserted into any appropriate expression vector. The necessary transcriptional and translational signals, including promoter/enhancer element, can derive from the native ALDO gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the ALDO gene product, the expression vector can comprise a promoter operably linked to an ALDO gene nucleic acid, one or more origins of replication, and, one or more selectable markers (e.g. thymidine kinase activity, resistance to antibiotics, etc.). Alternatively, recombinant expression vectors can be identified by assaying for the expression of the ALDO gene product based on the physical or functional properties of the ALDO protein in in vitro assay systems (e.g. immunoassays).

The ALDO protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the ALDO gene sequence is identified, the gene product can be isolated and purified using standard methods (e.g. ion exchange, affinity, and gel exclusion chromatography; centrifugation; differential solubility; electrophoresis). Alternatively, native ALDO proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of ALDO or other genes associated with the IGF pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter ALDO expression may be used in in vivo assays to test for activity of a candidate IGF modulating agent, or to further assess the role of ALDO in a IGF pathway process such as apoptosis or cell proliferation. Preferably, the altered ALDO expression results in a detectable phenotype, such as decreased or increased levels of cell proliferation, angiogenesis, or apoptosis compared to control animals having normal ALDO expression. The genetically modified animal may additionally have altered IGF expression (e.g. IGF knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 0.1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous ALDO gene that results in a decrease of ALDO function, preferably such that ALDO expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse ALDO gene is used to construct a homologous recombination vector suitable for altering an endogenous ALDO gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the ALDO gene, e.g., by introduction of additional copies of ALDO, or by operatively inserting a regulatory sequence that provides for altered expression of an endogenous copy of the ALDO gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the IGF pathway, as animal models of disease and disorders implicating defective IGF function, and for in vivo testing of candidate therapeutic agents, such as those identified in screens described below. The candidate therapeutic agents are administered to a genetically modified animal having altered ALDO function and phenotypic changes are compared with appropriate control animals such as genetically modified animals that receive placebo treatment, and/or animals with unaltered ALDO expression that receive candidate therapeutic agent.

In addition to the above-described genetically modified animals having altered ALDO function, animal models having defective IGF function (and otherwise normal ALDO function), can be used in the methods of the present invention. For example, a mouse with defective PTEN function can be used to assess, in vivo, the activity of a candidate PTEN modulating agent identified in one of the in vitro assays described below. Transgenic mice with defective PTEN function have been described in literature (Di Cristofano et al, supra). Preferably, the candidate IGF modulating agent when administered to a model system with cells defective in IGF function, produces a detectable phenotypic change in the model system indicating that the IGF function is restored, i.e., the cells exhibit normal cell cycle progression.

Modulating Agents

The invention provides methods to identify agents that interact with and/or modulate the function of ALDO and/or the IGF pathway. Modulating agents identified by the methods are also part of the invention. Such agents are useful in a variety of diagnostic and therapeutic applications associated with the IGF pathway, as well as in further analysis of the ALDO protein and its contribution to the IGF pathway. Accordingly, the invention also provides methods for modulating the IGF pathway comprising the step of specifically modulating ALDO activity by administering an ALDO-interacting or -modulating agent.

As used herein, an "ALDO-modulating agent" is any agent that modulates ALDO function, for example, an agent that interacts with ALDO to inhibit or enhance ALDO activity or otherwise affect normal ALDO function. ALDO function can be affected at any level, including transcription, protein expression, protein localization, and cellular or extra-cellular activity. In a preferred embodiment, the ALDO-modulating agent specifically modulates the function of the ALDO. The phrases "specific modulating agent", "specifically modulates", etc., are used herein to refer to modulating agents that directly bind to the ALDO polypeptide or nucleic acid, and preferably inhibit, enhance, or otherwise alter, the function of the ALDO. These phrases also encompass modulating agents that alter the interaction of the ALDO with a binding partner, substrate, or cofactor (e.g. by binding to a binding partner of an ALDO, or to a protein/binding partner complex, and altering ALDO function). In a further preferred embodiment, the ALDO-modulating agent is a modulator of the IGF pathway (e.g. it restores and/or upregulates IGF function) and thus is also a IGF-modulating agent.

Preferred ALDO-modulating agents include small molecule compounds; ALDO-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the ALDO protein or may be identified by screening compound libraries. Alternative appropriate modulators of this class are natural products, particularly secondary metabolites from organisms such as plants or fungi, which can also be identified by screening compound libraries for ALDO-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the IGF pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific ALDO-interacting proteins are useful in a variety of diagnostic and therapeutic applications related to the IGF pathway and related disorders, as well as in validation assays for other ALDO-modulating agents. In a preferred embodiment, ALDO-interacting proteins affect normal ALDO function, including transcription, protein expression, protein localization, and cellular or extra-cellular activity. In another embodiment, ALDO-interacting proteins are useful in detecting and providing information about the function of ALDO proteins, as is relevant to IGF related disorders, such as cancer (e.g., for diagnostic means).

An ALDO-interacting protein may be endogenous, i.e. one that naturally interacts genetically or biochemically with an ALDO, such as a member of the ALDO pathway that modulates ALDO expression, localization, and/or activity. ALDO-modulators include dominant negative forms of ALDO-interacting proteins and of ALDO proteins themselves. Yeast two-hybrid and variant screens offer preferred methods for identifying endogenous ALDO-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250: 1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An ALDO-interacting protein may be an exogenous protein, such as an ALDO-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). ALDO antibodies are further discussed below.

In preferred embodiments, an ALDO-interacting protein specifically binds an ALDO protein. In alternative preferred embodiments, an ALDO-modulating agent binds an ALDO substrate, binding partner, or cofactor.

Antibodies

In another embodiment, the protein modulator is an ALDO specific antibody agonist or antagonist. The antibodies have therapeutic and diagnostic utilities, and can be used in screening assays to identify ALDO modulators. The antibodies can also be used in dissecting the portions of the ALDO pathway responsible for various cellular responses and in the general processing and maturation of the ALDO.

Antibodies that specifically bind ALDO polypeptides can be generated using known methods. Preferably the antibody is specific to a mammalian ortholog of ALDO polypeptide, and more preferably, to human ALDO. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of ALDO which are particularly antigenic can be selected, for example, by routine screening of ALDO polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of an ALDO. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of ALDO or substantially purified fragments thereof. If ALDO fragments are used, they preferably comprise at least 10, and more preferably, at least 20 contiguous amino acids of an ALDO protein. In a particular embodiment, ALDO-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of ALDO-specific antibodies is assayed by an appropriate assay such as a solid phase enzyme-linked immunosorbant assay (ELISA) using immobilized corresponding ALDO polypeptides. Other assays, such as radioimmunoassays or fluorescent assays might also be used.

Chimeric antibodies specific to ALDO polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann LM, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

ALDO-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Nucleic Acid Modulators

Other preferred ALDO-modulating agents comprise nucleic acid molecules, such as antisense oligomers or double stranded RNA (dsRNA), which generally inhibit ALDO activity. Preferred nucleic acid modulators interfere with the function of the ALDO nucleic acid such as DNA replication, transcription, translocation of the ALDO RNA to the site of protein translation, translation of protein from the ALDO RNA, splicing of the ALDO RNA to yield one or more mRNA species, or catalytic activity which may be engaged in or facilitated by the ALDO RNA.

In one embodiment, the antisense oligomer is an oligonucleotide that is sufficiently complementary to an ALDO mRNA to bind to and prevent translation, preferably by binding to the 5' untranslated region. ALDO-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphordiamidate intersubunit linkages. Details of how to make and use PMOs and other antisense oligomers are well known in the art (e.g. see WO99/ 18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred ALDO nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178; Hsieh AC et al. (2004) NAR 32(3):893-901).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, an ALDO-specific nucleic acid modulator is used in an assay to further elucidate the role of the ALDO in the IGF pathway, and/or its relationship to other members of the pathway. In another aspect of the invention, an ALDO-specific antisense oligomer is used as a therapeutic agent for treatment of IGF-related disease states.

Assay Systems

The invention provides assay systems and screening methods for identifying specific modulators of ALDO activity. As used herein, an "assay system" encompasses all the components required for performing and analyzing results of an assay that detects and/or measures a particular event. In general, primary assays are used to identify or confirm a modulator's specific biochemical or molecular effect with respect to the ALDO nucleic acid or protein. In general, secondary assays further assess the activity of an ALDO modulating agent identified by a primary assay and may confirm that the modulating agent affects ALDO in a manner relevant to the IGF pathway. In some cases, ALDO modulators will be directly tested in a secondary assay.

In a preferred embodiment, the screening method comprises contacting a suitable assay system comprising an ALDO polypeptide or nucleic acid with a candidate agent under conditions whereby, but for the presence of the agent, the system provides a reference activity (e.g. aldolase activity), which is based on the particular molecular event the screening method detects. A statistically significant difference between the agent-biased activity and the reference activity indicates that the candidate agent modulates ALDO activity, and hence the IGF pathway. The ALDO polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam GS et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of ALDO and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when ALDO-interacting proteins are used in screens to identify small molecule modulators, the binding specificity of the interacting protein to the ALDO protein may be assayed by various known methods such as substrate processing (e.g. ability of the candidate ALDO-specific binding agents to function as negative effectors in ALDO-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit ALDO specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of an ALDO polypeptide, a fusion protein thereof, or to cells or membranes bearing the polypeptide or fusion protein. The ALDO polypeptide can be full length or a fragment thereof that retains functional ALDO activity. The ALDO polypeptide may be fused to another polypeptide, such as a peptide tag for detection or anchoring, or to another tag. The ALDO polypeptide is preferably human ALDO, or is an ortholog or derivative thereof as described above. In a preferred embodiment, the screening assay detects candidate agent-based modulation of ALDO interaction with a binding target, such as an endogenous or exogenous protein or other substrate that has ALDO-specific binding activity, and can be used to assess normal ALDO gene function.

Suitable assay formats that may be adapted to screen for ALDO modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes PB, supra; Hertzberg R P and Pope A J, Curr Opin Chem Biol (2000) 4:445-451).

A variety of suitable assay systems may be used to identify candidate ALDO and IGF pathway modulators (e.g. U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

High throughput X-ray crystallographic screening assays for aldolase enzymes have been described (Sanders et al (2004) J Med Chem. 47:1709-18).

Apoptosis assays. Apoptosis or programmed cell death is a suicide program that is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available APO-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as ARRAYSCAN® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses an ALDO, and that optionally has defective IGF function (e.g. IGF is over-expressed or under-expressed relative to wild-type cells). A test agent can be added to the apoptosis assay system and changes in induction of apoptosis relative to controls where no test agent is added, identify candidate IGF modulating agents. In some embodiments of the invention, an apoptosis assay may be used as a secondary assay to test a candidate IGF modulating agents that is initially identified using a cell-free assay system. An apoptosis assay may also be used to test whether ALDO function plays a direct role in apoptosis. For example, an apoptosis assay may be performed on cells that over- or under-express ALDO relative to wild type cells. Differences in apoptotic response compared to wild type cells suggests that the ALDO plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin SL et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CELLTITER 96® AQueous Non-Radioactive Cell Proliferation Assay (Cat.# G5421).

Cell proliferation may also be assayed by colony formation in soft agar, or clonogenic survival assay (Sambrook et al., Molecular Cloning, Cold Spring Harbor (1989)). For example, cells transformed with ALDO are seeded in soft agar plates, and colonies are measured and counted after two weeks incubation.

Cell proliferation may also be assayed by measuring ATP levels as indicator of metabolically active cells. Such assays are commercially available, for example CELL TITER-GLO™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with an ALDO may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses an ALDO, and that optionally has defective IGF function (e.g. IGF is over-expressed or under-expressed relative to wild-type cells). A test agent can be added to the assay system and changes in cell proliferation or cell cycle relative to controls where no test agent is added, identify candidate IGF modulating agents. In some embodiments of the invention, the cell proliferation or cell cycle assay may be used as a secondary assay to test a candidate IGF modulating agents that is initially identified using another assay system such as a cell-free assay system. A cell proliferation assay may also be used to test whether ALDO function plays a direct role in cell proliferation or cell cycle. For example, a cell proliferation or cell cycle assay may be performed on cells that over- or under-express ALDO relative to wild type cells. Differences in proliferation or cell cycle compared to wild type cells suggests that the ALDO plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses an ALDO, and that optionally has defective IGF function (e.g. IGF is over-expressed or under-expressed relative to wild-type cells). A test agent can be added to the angiogenesis assay system and changes in angiogenesis relative to controls where no test agent is added, identify candidate IGF modulating agents. In some embodiments of the invention, the angiogenesis assay may be used as a secondary assay to test a candidate IGF modulating agents that is initially identified using another assay system. An angiogenesis assay may also be used to test whether ALDO function plays a direct role in cell proliferation. For example, an angiogenesis assay may be performed on cells that over- or under-express ALDO relative to wild type cells. Differences in angiogenesis compared to wild type cells suggest that the ALDO plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with ALDO in hypoxic conditions (such as with 0.1% $O_2$, 5% $CO_2$, and balance $N_2$, generated in a NAPCO® 7001 incubator (Precision Scientific)) and normoxic conditions, followed by assessment of gene activity or expression by TAQMAN®. For example, a hypoxic induction assay system may comprise a cell that expresses an ALDO, and that optionally has, defective IGF function (e.g. IGF is over-expressed or under-expressed relative to wild-type cells). A test agent can be added to the hypoxic induction assay system and changes in hypoxic response relative to controls where no test agent is added, identify candidate IGF modulating agents. In some embodiments of the invention, the hypoxic induction assay may be used as a secondary assay to test a candidate IGF modulating agents that is initially identified using another assay system. A hypoxic induction assay may also be used to test whether ALDO function plays a direct role in the hypoxic response. For example, a hypoxic induction assay may be performed on cells that over- or under-express ALDO relative to wild type cells. Differences in hypoxic response compared to wild type cells suggest that the ALDO plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the ALDO protein. Methods for testing antibody affinity and specificity are well known in the art (Harlow and Lane, 1988, 1999, supra). The enzyme-linked immunosorbant assay (ELISA) is a preferred method for detecting ALDO-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance ALDO gene expression, preferably mRNA expression. In general, expression analysis comprises comparing ALDO expression in like populations of cells (e.g., two pools of cells that endogenously or recombinantly express ALDO) in the presence and absence of the nucleic acid modulator. Methods for analyzing mRNA and protein expression are well known in the art. For instance, Northern blotting, slot blotting, ribonuclease protection, quantitative RT-PCR (e.g. using the TAQMAN®, PE APPLIED BIOSYSTEMS®), or microarray analysis may be used to confirm that ALDO mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the ALDO protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve ALDO mRNA expression, may also be used to test nucleic acid modulators.

Secondary Assays

Secondary assays may be used to further assess the activity of ALDO-modulating agent identified by any of the above methods to confirm that the modulating agent affects ALDO in a manner relevant to the IGF pathway. As used herein, ALDO-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with ALDO.

Secondary assays generally compare like populations of cells or animals (e.g., two pools of cells or animals that endogenously or recombinantly express ALDO) in the presence and absence of the candidate modulator. In general, such assays test whether treatment of cells or animals with a candidate ALDO-modulating agent results in changes in the IGF pathway in comparison to untreated (or mock- or placebo-treated) cells or animals. Certain assays use "sensitized genetic backgrounds", which, as used herein, describe cells or animals engineered for altered expression of genes in the IGF or interacting pathways.

Cell-Based Assays

Cell based assays may detect endogenous IGF pathway activity or may rely on recombinant expression of IGF pathway components. Any of the aforementioned assays may be used in this cell-based format. Candidate modulators are typically added to the cell media but may also be injected into cells or delivered by any other efficacious means.

Animal Assays

A variety of non-human animal models of normal or defective IGF pathway may be used to test candidate ALDO modulators. Models for defective IGF pathway typically use genetically modified animals that have been engineered to mis-express (e.g., over-express or lack expression in) genes involved in the IGF pathway. Assays generally require systemic delivery of the candidate modulators, such as by oral administration, injection, etc.

In a preferred embodiment, IGF pathway activity is assessed by monitoring neovascularization and angiogenesis. Animal models with defective and normal IGF are used to test the candidate modulator's effect on ALDO in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which over-express the ALDO. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on ALDO is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the ALDO endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorigenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorigenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorigenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorigenicity and modulator efficacy can be evaluating life-span extension and/or tumor characteristics, including number of tumors, tumor size, tumor morphology, vessel density, apoptotic index, etc.

Diagnostic and Therapeutic Uses

Specific ALDO-modulating agents are useful in a variety of diagnostic and therapeutic applications where disease or disease prognosis is related to defects in the IGF pathway, such as angiogenic, apoptotic, or cell proliferation disorders. Accordingly, the invention also provides methods for modulating the IGF pathway in a cell, preferably a cell pre-determined to have defective or impaired IGF function (e.g. due to overexpression, underexpression, or misexpression of IGF, or due to gene mutations), comprising the step of administering an agent to the cell that specifically modulates ALDO activity. Preferably, the modulating agent produces a detectable phenotypic change in the cell indicating that the IGF function is restored. The phrase "function is restored", and equivalents, as used herein, means that the desired phenotype is achieved, or is brought closer to normal compared to untreated cells. For example, with restored IGF function, cell proliferation and/or progression through cell cycle may normalize, or be brought closer to normal relative to untreated cells. The invention also provides methods for treating disorders or disease associated with impaired IGF function by administering a therapeutically effective amount of an ALDO-modulating agent that modulates the IGF pathway. The invention further provides methods for modulating ALDO function in a cell, preferably a cell predetermined to have defective or impaired ALDO function, by administering an ALDO-modulating agent. Additionally, the invention provides a method for treating disorders or disease associated with impaired ALDO function by administering a therapeutically effective amount of an ALDO-modulating agent.

The discovery that ALDO is implicated in IGF pathway provides for a variety of methods that can be employed for the diagnostic and prognostic evaluation of diseases and disorders involving defects in the IGF pathway and for the identification of subjects having a predisposition to such diseases and disorders.

Various expression analysis methods can be used to diagnose whether ALDO expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective IGF signaling that express an ALDO, are identified as amenable to treatment with an ALDO modulating agent. In a preferred application, the IGF defective tissue overexpresses an ALDO relative to normal tissue. For example, a Northern blot analysis of mRNA from tumor and normal cell lines, or from tumor and matching normal tissue samples from the same patient, using full or partial ALDO cDNA sequences as probes, can determine whether particular tumors express or overexpress ALDO. Alternatively, the TAQMAN® is used for quantitative RT-PCR analysis of ALDO expression in cell lines, normal tissues and tumor samples (PE APPLIED BIOSYSTEMS®).

Various other diagnostic methods may be performed, for example, utilizing reagents such as the ALDO oligonucleotides, and antibodies directed against an ALDO, as described above for: (1) the detection of the presence of ALDO gene mutations, or the detection of either over- or under-expression of ALDO mRNA relative to the non-disorder state; (2) the detection of either an over- or an under-abundance of ALDO gene product relative to the non-disorder state; and (3) the detection of perturbations or abnormalities in the signal transduction pathway mediated by ALDO.

Kits for detecting expression of ALDO in various samples, comprising at least one antibody specific to ALDO, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in ALDO expression, the method comprising: a) obtaining a biological sample from the patient; b) contacting the sample with a probe for ALDO expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* Cell IGF Screen

RNA interference (RNAi) was used to create dPTEN-deficient cultured *Drosophila* cells (Schneider S2 cells (Schneider, I. (1972) J. Embryol. Exp. Morph. 27, 363), adapted to serum-free media, from Invitrogen Corp., Carlsbad, Calif.). Cells were treated for 3 days with dPTEN double stranded RNA (dsRNA) or a control dsRNA representing sequences from a Renilla luciferase cDNA. After a 3 day dsRNA pretreatment, 1 µM bovine insulin was added to cells treated with dPTEN dsRNA to provide additional stimulation of the IGF/insulin pathway. PTEN-deficient, insulin-stimulated cells and control cells were plated in 384-well format and dsRNA representing approximately 10,000 different *Drosophila* genes were added to individual wells. A cell proliferation assay (AQUEOUS ONE™ assay—Promega Corp, Madison, Wis.) was used to quantify cell viability after 96-hours incubation. For each of the greater than 6000 dsRNA sequences tested in this manner, cell viability data was obtained on dPTEN-deficient, insulin-stimulated cells (insulin and dPTEN dsRNA-treated) and control cells (Renilla luciferase dsRNA-treated). Comparison of this data for each dsRNA identified dsRNA sequences that preferentially reduced the viability of insulin and dPTEN dsRNA treated cells. Additionally, the screen identified sequences that when inactivated, preferentially suppressed insulin induced LDH (lactate dehydrogenase) expression relative to normal cells. The LDH expression levels were detected by TAQMAN® analysis.

Dmel cells were treated with 1 µM bovine insulin to stimulate the IGF/insulin pathway. The insulin-stimulated cells were plated into 384-well plates and dsRNA representing approximately 10,000 different Drosophila genes were added to individual wells. After a 96-hour incubation cells were lysed using Cells-to-cDNAII cell lysis buffer (AMBION®) and a 384 format, multiplexed, RT-PCR TAQMAN® assay was run on the lysates. The TAQMAN® assay identifies changes in expression of lactate dehydrogenase, an IGF reporter gene, and Rp49, an internal standard to normalize values for cell number and RT-PCR efficiency. For each of the greater than 13,000 dsRNA sequences tested in this manner, effects on LDH and rp49 expression were analyzed. Selections of genes with the greatest reduction in LDH expression were further analyzed in a multiplexed Western Blot assay that examines phosphorylation and overall levels of several proteins simultaneously. The multiplexed assay measured changes in phosphorylation of 4E-BP 1 (Thr37/46), MAPK1 (Thr202/Tyr204) and either S6K(Thr389) phosphorylation or total RPS6 protein levels. The multiplexed Western assay was done on lysates from cells treated with 1 µM insulin plated in 96 format and treated with target dsRNA for 96 hrs. Each lysate was tested for its differences in phosphorylation of 4E-BP1 (Thr37/46), MAPK1 (Thr202/Tyr204), and either S6K(Thr389) phosphorylation or total RPS6 protein relative to negative control dsRNA (luciferase dsRNA). The quantitative Western blot assay, like the LDH reporter assay, was validated as a readout for IGF signaling by RNAi of known pathway components. DROSOPHILA ALD was identified as a suppressor in the screen. Orthologs of the modifier are referred to herein as ALDO.

BLAST analysis (Altschul et al., supra) was employed to identify orthologs of Drosophila modifiers. For example, representative sequences from ALDO, GI#s 4557305 (SEQ ID NO:13), 40354205 (SEQ ID NO:14), and 4885063 (SEQ ID NO:15) share 67%, 61%, and 68% amino acid identity, respectively, with the Drosophila ALD.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 January 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the Caenorhabditis elegans genome and identification of human orthologs. Genome Res. 2000 November; 10(11):1679-89) programs. For example, the Fructose-bisphosphate aldolase domain (PFAM 00274) of ALDO from GI#s 4557305, 40354205, and 4885063 (SEQ ID NOs:13, 14, and 15, respectively) is located respectively at approximately amino acid residues 15-364, 15-364, and 15-364.

II. High-Throughput In Vitro Fluorescence Polarization Assay

Fluorescently-labeled ALDO peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of ALDO activity.

III. High-Throughput In Vitro Binding Assay.

$^{33}$P-labeled ALDO peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate IGF modulating agents.

IV. Immunoprecipitations and Immunoblotting

For coprecipitation of transfected proteins, $3 \times 10^6$ appropriate recombinant cells containing the ALDO proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 mil of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC$^{SM}$(American Type Culture Collection, Manassas, Va. 20110-2209). Normal and tumor tissues were obtained from Impath, UC Davis, CLONTECH™, STRATAGENE®, Ardais, Genome Collaborative, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/µl. Single stranded cDNA was then synthesized by reverse transcribing the RNA samples using random hexamers and 500 ng of total RNA per reaction, following protocol 430-4965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product. Expression analysis was performed using a 7900HT instrument.

TAQMAN® reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all, normal samples (i.e., Tumor-average (all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| | Gene Name | | |
|---|---|---|---|
| | ALDOA | ALDOB | ALDOC |
| | | SEQ ID NO | |
| | 1 | 6 | 10 |
| Breast | 39% | 6% | 8% |
| # of Pairs | 36 | 16 | 36 |
| Colon | 15% | 55% | 30% |
| # of Pairs | 40 | 40 | 40 |
| Head And Neck | 31% | 0% | 54% |
| # of Pairs | 13 | 1 | 13 |
| Liver | 56% | 0% | 0% |
| # of Pairs | 9 | 9 | 9 |
| Lung | 48% | 29% | 52% |
| # of Pairs | 40 | 28 | 40 |
| Lymphoma | 0% | 0% | 0% |
| # of Pairs | 4 | 4 | 4 |
| Ovary | 58% | 25% | 16% |
| # of Pairs | 19 | 8 | 19 |
| Pancreas | 75% | 42% | 67% |
| # of Pairs | 12 | 12 | 12 |
| Prostate | 0% | 38% | 0% |
| # of Pairs | 24 | 8 | 24 |

TABLE 1-continued

| | Gene Name | | |
|---|---|---|---|
| | ALDOA | ALDOB | ALDOC |
| | | SEQ ID NO | |
| | 1 | 6 | 10 |
| Skin | 43% | 0% | 29% |
| # of Pairs | 7 | 5 | 7 |
| Stomach | 55% | 9% | 27% |
| # of Pairs | 11 | 11 | 11 |
| Testis | 50% | 25% | 12% |
| # of Pairs | 8 | 4 | 8 |
| Thyroid Gland | 21% | 50% | 43% |
| # of Pairs | 14 | 4 | 14 |
| Uterus | 35% | 27% | 4% |
| # of Pairs | 23 | 15 | 23 |

VI. ALDO Functional Assays

RNAi experiments were carried out to knock down expression of ALDO (SEQ ID NO: 1) in various cell lines using small interfering RNAs (siRNA, Elbashir et al, supra).

Effect of ALDO RNAi on cell proliferation and growth. BrdU and Cell TITERGLO™ assays, as described above, were employed to study the effects of decreased ALDO expression on cell proliferation. The results of these experiments indicated that RNAi of ALDO decreased proliferation in A549 lung cancer cells.

[$^3$H]-thymidine incorporation assay, as described above, was also employed to study the effects of decreased ALDO expression on cell proliferation. The results of this experiment indicated that RNAi of ALDO decreased proliferation in A2780 ovarian cancer and A549 lung cancer cells.

Effect of ALDO RNAi on apoptosis. The Phospho-histone H2B assay, as described above, was employed to study the effects of decreased ALDO expression on apoptosis. The results of this experiment indicated that RNAi of ALDO increased apoptosis in 231T breast cancer cells and A549 lung cancer cells.

Multiple parameter apoptosis assay, as described above, was also used to study the effects of decreased ALDO expression on apoptosis. The results of this experiment indicated that RNAi of ALDO increased apoptosis in A2780 ovarian cancer and A549 lung cancer cells.

Transcriptional reporter assays. Transcriptional reporter assay was performed to measure the effects of overexpressed ALDO on expression of various transcription factors. In this assay, rat intestinal epithelial cells (RIEs) or NIH3T3 cells were co-transfected with reporter constructs containing various transcription factors and luciferase along with ALDO. Luciferase intensity was then measured as the readout for transcriptional activation due to overexpression of the ALDO. Overexpressed ALDO caused an increased expression of the EGR (early growth response) transcription factor.

Involvement in PTEN/IGF pathway: ALDO FOXO nuclear translocation assays. FOXO nuclear translocation assays, as described above, were employed to assess involvement of ALDO in the PTEN/IGF pathway. In these experiments, cells with reduced expression of ALDO by RNAi were transiently transfected with a plasmid expressing GFP-tagged FOXO. Automated imaging of cellular components, such as nucleus and cytoplasm were then carried out to assess translocation of FOXO. Alternatively, cells were co-transfected with siRNA directed to ALDO along with a plasmid containing FOXO, and a cassette containing a promoter, a FOXO response element, and luciferase. Cells were then analyzed for luciferase activity and compared with cells with no siRNA. Results indicated that reduced expression of ALDO led to retention of FOXO in the nucleus, similar to a reduced AKT effect. These results suggest involvement of ALDO in the PTEN/IGF pathway.

Pan-AKT assays. This assay was developed to detect involvement of ALDO in the PTEN/IGF pathway. The assay detects changes in phosphorylation for several substrates of AKT, such as PRAS40, BAD, 4EBP1, and RPS6. For this experiment, antibodies were raised against phosphorylated AKT substrates, including the consensus phosphorylated AKT substrate sequence RxRxxS/T. Expression levels of phosphorylated substrates were then quantitated at normal levels, in presence of a negative control, a positive control (AKT), and then with ALDO knockout. For example, when AKT levels were reduced, expression of all its substrates was also reduced. Results indicated that reduced expression of ALDO was similar to reduced AKT levels in 231T breast cancer and A549 lung cancer cells.

We used RPS6 assay for one subset of experiments. RPS6 is an IGF dependent substrate of AKT. IGF1 treatment increases cytoplasmic RPS6 levels. Alternatively, Lily compound LY294002, a PI3K inhibitor, reduces AKT and cytoplasmic RPS6 levels. Cells were plated in 96 well plates, transfected with RNAi for ALDO, fixed, treated with RPS6 antibody, and stained. Measurements were based on percentage of population of cells with increased or decreased staining compared with negative or positive control cells. Results of this experiment showed that reduced expression of ALDO altered the level of phospho RPS6 protein in 231T breast cancer cells, A549 lung cancer cells, and PC3 prostate cancer cells, thus suggesting an involvement in the IGF pathway.

We used PRAS40 as the substrate for another subset of experiments. For this substrate, pathway inhibition causes decreased cytoplasmic staining and increased nuclear and perinuclear staining. Cells were plated in 96 well plates, transfected with RNAi for ALDO, fixed, treated with PRAS40 antibody, and stained. Measurements were based on percentage of population of cells with increased or decreased nuclear/cytoplasmic staining ratio compared with negative or positive control cells. Results of this experiment showed that reduced expression of ALDO altered the level of phospho PRAS40 protein in A549 lung cancer and PC3 prostate cancer cells, thus again suggesting an involvement in the IGF pathway.

We used BAD as the substrate for another subset of the experiments. For this substrate, AKT pathway inhibition causes decreased cytoplasmic staining and unchanged or increased nuclear staining. Cells were plated in 96 well plates, transfected with RNAi for ALDO, fixed, permeabilized and stained with anti-phospho-BAD antibody. Measurements were based on the percentage of the population of cells with a decreased Cytoplasmic/Nuclear staining ratio compared with negative or positive control cells. Results of this experiment showed that reduced expression of ALDO caused a reduction in the level of phospho-BAD protein in the cytoplasm in 231T breast cancer and PC3 prostate cancer cells, thus again suggesting an involvement in the IGF pathway. Taken together, the results of the pan-AKT assay suggest involvement of ALDO in the PTEN/IGF pathway.

What is claimed is:

1. A method of identifying a candidate Insulin-Like Growth Factor (IGF) pathway modulating agent, said method comprising the steps of:
   (a) providing an assay system comprising a cell in culture that has defective IGF pathway function and expresses a fructose 1, 6 bisphosphate aldolase (ALDO) polypeptide or nucleic acid, wherein the ALDO nucleic acid comprises SEQ ID NO: 1 and the ALDO polypeptide is encoded by a nucleic acid comprising SEQ ID NO: 1;
   (b) contacting the assay system with a test agent that modulates the expression of ALDO; and
   (c) detecting a change in the assay system in the presence of the test agent of step (b) as compared to the absence of the test agent, wherein the detection of a change in the assay system identifies the test agent as a candidate IGF pathway modulating agent.

2. The method of claim 1, wherein the defect in IGF pathway function is defective Phosphatase and Tensin homolog deleted on Chromosome 10 (PTEN) function.

3. The method of claim 1, wherein the assay system includes a screening assay comprising an ALDO polypeptide, and the candidate test agent is a small molecule modulator.

4. The method of claim 3, wherein the screening assay is an aldolase assay.

5. The method of claim 1, wherein the assay system is selected from the group consisting of an apoptosis assay system, a cell proliferation assay system, an angiogenesis assay system, and a hypoxic induction assay system.

6. The method of claim 1, wherein the assay system includes a binding assay comprising an ALDO polypeptide and the candidate test agent is an antibody.

7. The method of claim 1, wherein the assay system includes an expression assay comprising an ALDO nucleic acid and the candidate test agent is a nucleic acid modulator.

8. The method of claim 7, wherein the nucleic acid modulator is an antisense oligomer.

9. The method of claim 7, wherein the nucleic acid modulator is a phosphothioate morpholino oligomer (PMO).

10. The method of claim 1 additionally comprising:
    (d) administering the candidate IGF pathway modulating agent identified in step (c) to a model system comprising cells defective in IGF function and detecting a phenotypic change in the model system that indicates that the IGF function is restored.

11. The method of claim 10, wherein the model system is a mouse model with defective IGF function.

12. The method of claim 1, comprising the additional steps of:
    (d) providing a second assay system capable of detecting a change in the IGF pathway comprising cultured cells or a non-human animal that express an ALDO polypeptide or nucleic acid,
    (e) contacting the second assay system with the test agent of step (b); and
    (f) determining a change in the IGF pathway in the second assay system, wherein a change in the IGF pathway between the presence and absence of said test agent confirms the test agent as a candidate IGF pathway modulating agent.

13. The method of claim 12, wherein the second assay system comprises cultured cells.

14. The method of claim 12, wherein the second assay system comprises a non-human animal.

15. The method of claim 14, wherein the non-human animal mis-expresses a IGF pathway gene.

* * * * *

SEQUENCE LISTING

```
<160> NUMBER OF SEQ ID NOS: 15

<210> SEQ ID NO 1
<211> LENGTH: 2353
<212> TYPE: DNA
<213> ORGANISM: Homo sapiens

<400> SEQUENCE: 1
cctagcttgg cgcggaatcc gtgaattgcc cgcggcccga gggtgcagct cccggactga      60
ctggctctgc ccttccccat ggacgcctcc tctagcccgt ggaatccaac cccggctcct     120
gtcagcagcc ctcccctgct gctccccatc cctgccatcg tcttcatcgc tgtgggcatc     180
tatttgttgc tgctgggtct agtcctgctg actaggaact gcctgctggc ccaggctgc      240 tgcgcggacg gtagctcccc ctgcaggaag caaggttcct ccgggccccc agactgctgc     300
tggacctgtg cagaagcctg caactttcct ctgcctagcc cggcccactt cctggatgct     360
tgctgccccc agcccaccag agctgactgg gcacctcgct gccccgctg ctgcccactc      420 tgcgactgtg cctgtacgtg ccagctcccc gactgccaga gcctcaactg tctctgcttc     480
gagatcaagc tccgatgagg acccagggcc cctgccctct ggggagcggc cagccccag      540 ggcccatgtg ccctcctccc tgaagagcct ttccccacgc cactggaacc acagatggcc     600
tgccgagcac ccaggcctgg gaactggaag tggcagcgca gggcctggct ccctgcaggg     660
caggactctt ggccggctgg acggcagctc ctctggaggg ccagaaaaga gagggctag      720 tgctcgggca ggtgccctgg cttcccttcc cctccacacg tcaacgattc tatttgaagt     780
tgggcagggg ggtggcgctg ctcaccacac acaagtgtta taggaggagt ctggcccttg     840
agtaccgggt acgcaggggt gcctcaacca cactccgtcc acggactctc cgttatttta     900
```

```
ggaggtccct ggccaaagat ttatttctct tgacaaccaa gggcctccgt ctggatttcc    960
aaggaagaat ttcctctgaa gcaccggaac ttgctactac cagcaccatg ccctaccaat   1020
atccagcact gaccccggag cagaagaagg agctgtctga catcgctcac cgcatcgtgg   1080
cacctggcaa gggcatcctg gctgcagatg agtccactgg gagcattgcc aagcggctgc   1140
agtccattgg caccgagaac accgaggaga accggcgctt ctaccgccag ctgctgctga   1200
cagctgacga ccgcgtgaac ccctgcattg ggggtgtcat cctcttccat gagacactct   1260
accagaaggc ggatgatggg cgtcccttcc cccaagttat caaatccaag ggcggtgttg   1320
tgggcatcaa ggtagacaag ggcgtggtcc cctggcaggg acaaatggcg agactacca   1380
cccaagggtt ggatgggctg tctgagcgct gtgcccagta caagaaggac ggagctgact   1440
tcgccaagtg gcgttgtgtg ctgaagattg ggaacacac cccctcagcc ctcgccatca   1500
tggaaaatgc caatgttctg gcccgttatg ccagtatctg ccagcagaat ggcattgtgc   1560
ccatcgtgga gcctgagatc ctccctgatg gggaccatga cttgaagcgc tgccagtatg   1620
tgaccgagaa ggtgctggct gctgtctaca aggctctgag tgaccaccac atctacctgg   1680
aaggcacctt gctgaagccc aacatggtca ccccaggcca tgcttgcact cagaagtttt   1740
ctcatgagga gattgccatg gcgaccgtca cagcgctgcg ccgcacagtg cccccgctg   1800
tcactgggat caccttcctg tctggaggcc agagtgagga ggaggcgtcc atcaacctca   1860
atgccattaa caagtgcccc ctgctgaagc cctgggccct gaccttctcc tacggccgag   1920
ccctgcaggc ctctgccctg aaggcctggg gcgggaagaa ggagaacctg aaggctgcgc   1980
aggaggagta tgtcaagcga gccctggcca acagccttgc ctgtcaagga aagtacactc   2040
cgagcggtca ggctggggct gctgccacgc agtccctctt cgtctctaac cacgcctatt   2100
aagcggaggt gttcccaggc tgcccccaac actccaggcc ctgcccctc ccactcttga   2160
agaggaggcc gcctcctcgg ggctccaggc tggcttgccc gcgctctttc ttccctcgtg   2220
acagtggtgt gtggtgtcgt ctgtgaatgc taagtccatc acccttccg gcacactgcc   2280
aaataaacag ctatttaagg gggaaaaaaa aaaaaaaaaa aaaaaaaaaa aaaaaaaaaa   2340
aaaaaaaaaa aaa                                                      2353

<210> SEQ ID NO 2
<211> LENGTH: 547
<212> TYPE: DNA
<213> ORGANISM: Homo sapiens

<400> SEQUENCE: 2
ggcaggggag gtagggaaca tttccctgac ctccaggaga ggggccctgc tcatcgggag     60
atgatgggaa accctagcta actagtcctt cccctctgtt tcctgtatcc aggaacttgc    120
tactaccagc accatgccct accaatatcc agcactgacc ccggagcaga agaaggagct    180
gtctgacatc gctcaccgca tcgtggcacc tggcaagggc atcctggctg cagatgagtc    240
cactggtgcg ggcaggagac agaatgggtg gagggtgcag ggttgggagt ggcaggctga    300
tccccctaatt cccatgtgac actcccaggg agcattgcca agcggctgca gtccattggc    360
accgagaaca ccgaggagaa ccggcgcttc taccgccagc tgctgctgac agctgacgac    420
cgcgtgaacc cctgcattgg gggtgtcatc ctcttccatg agacactcta ccagaaggcg    480
gatgatgggc gtcccttccc ccaagttatc aaatccaagg gcggtgttgt gggcatcaag    540
gtaaggg                                                              547

<210> SEQ ID NO 3
```

<211> LENGTH: 7530
<212> TYPE: DNA
<213> ORGANISM: Homo sapiens

<400> SEQUENCE: 3

| | | | | | |
|---|---|---|---|---|---|
| cacgcctgta | gttcagctac | tcagaaggct | aggcagaact | acttgaaccc | agagtggagg | 60 |
| ttgcagtgag | ccaagatcgc | accattgcac | tccaccctgg | gcaacagagt | gagaccctgt | 120 |
| ctcaaaaaaa | aaaaaaaatt | aaaaataggt | aaattccatt | ttcaaagata | cctgtaaaga | 180 |
| ttttaaaat | cattcatgaa | tgcggtctgt | tcgttgcaca | gagtagatgc | tcaaaaatgg | 240 |
| tgaatgagac | cctctatttt | ggtctcatgc | tgaagaagtc | cataaagccc | acaagtcatt | 300 |
| ttcatgatgg | acagaaaaat | gtgtgtgctt | tctctgtcta | ctgcctcaac | tgcacagacc | 360 |
| ccgggactgt | agcagaacca | tcttttgagc | ttgacaccgg | gaggcccaaa | ttctagcacg | 420 |
| ggacctaggg | ccagttgctc | tctggtcctc | agtctcctca | cccataaaat | gggaaggaga | 480 |
| gaaccctgaa | tcattgcttc | tagcttctga | actcagttgt | tcagaacaag | gactcactgc | 540 |
| tgattttca | acagcacagg | gaattgcact | gttcctggaa | tgatggacag | taccctctgt | 600 |
| tccactgggc | aagtgagatt | tcccaggcct | ctctgttccc | ttctcccctt | agagagcaac | 660 |
| agacgtgtgg | ccccaccacc | tccctcaacc | ctctctctcc | tccctcagga | ctgggcacct | 720 |
| cgctgccccc | gctgctgccc | actctgcgac | tgtgccagct | ccccgactgc | | 780 |
| cgagacctca | actgtctctg | cttcgagatc | aagctccata | ggacccaggc | cctgcctct | 840 |
| ggggagcggc | cagcccccag | gcccatgtgc | cctcctccct | gaagagcctt | tccccacgcc | 900 |
| actggaacca | cagatggcct | gccgagcacc | caggcctggg | aactggaatg | cagcgcagg | 960 |
| gcctggctcc | tgcagggcag | gactcttggc | cggctggacg | gcagctcctc | tggagggcca | 1020 |
| gaaaagagag | ggctagtgct | cggcagtgcc | ctgcttccct | tcccctccac | acgtcaacga | 1080 |
| ttctatttga | agttgggcag | ggggtggcgc | tgctcaccac | acacaagtgt | tataggagga | 1140 |
| gtctggcccc | gtagtaccgg | gtacgcaggg | gtgcctcaac | cacactccgt | ccacggactc | 1200 |
| tccgttattt | taggaggtag | atgtagtgcc | agtatctact | ctccttctta | aaaaaaacca | 1260 |
| gggctccaga | gaatcagaac | agccaccatc | accgcaggga | gtcaagggag | gagggagatt | 1320 |
| agagaaggag | ccagggaggg | tggcaggag | gccacgtgat | ccgagtcccc | tcaccccttt | 1380 |
| ccttcccaca | ggtccctggc | caaagattta | tttctcttga | caaccaaggg | cctccgtctg | 1440 |
| gatttccaag | gaagaatttc | ctctgaagca | ccggtgagtg | ggcaggggct | ctttgtcccc | 1500 |
| aatcaatcag | ggccgaccca | agtcttcctc | cccttcccc | atgccgggcc | ccacgatagt | 1560 |
| gtgaatgtca | ggggcttcag | gtttccctaa | atataggtcc | ctgccagagg | atccgtggcg | 1620 |
| ggaaagggc | agggtcatt | agagaagatc | ggggacacat | gtgggctgg | gcaggagctg | 1680 |
| ccttataacc | acccgggaac | ccctagctca | ctcgctgctg | accaggctct | gccggctcct | 1740 |
| tgccctcgcc | gcaggtgggc | cccttgcagg | accggccggg | tgggatgggt | tggaattggg | 1800 |
| ccaacaggtc | cagatgggtc | caggtaggag | gggagatttg | gacgatagga | gcagggggct | 1860 |
| cagcatctgg | gaggcagatc | agttcgggga | cggattttct | tttggagaag | gaagtcaggc | 1920 |
| tcaaggaaga | cgtttggcag | gaactgtgac | cccgcatgcc | agaggccgag | cagcggccgt | 1980 |
| gcatagccgc | gcattctggt | tttctgtggc | gcagaggact | accagcctgg | ctgcggcggc | 2040 |
| ccggcggaga | ccgccaccat | gcgcgaccca | gcccgcctgc | cagcctggaa | ctcggatggg | 2100 |
| gaggtctgcc | tccgcgcgcc | gctagttttcc | gaccgccttc | tcgctcccct | gctgtcctct | 2160 |
| cgatgcccctt | tcctccgcct | cccttgacgc | ctgggccagt | gacaggtgtc | gtccgcgccg | 2220 |

```
attcagcccg cgggcgaggc agctaacgca cgactgcgcg atgtggcccc tatggtgaca    2280
cgctgcagcc gcgaagaccg gaagctgggg ccccgggccg cgcgcgctgg gcctgggagg    2340
cgaaactcag cttccttcgt ttccgacttt tccatccgcg tcctccactt ccccgttccg    2400
ccctccccca ttgccaacat tctggctgag atcagcgccc agagcgcgcc aggctggggg    2460
aaaggagcag aagggagggc cctagcgacc cgcgggatgt ggtccgagtc acgtccgagg    2520
gggtggggag ggatcgtgtt ctcgcgcccg ccccttccta gcgcggcctc tggctcgcct    2580 ctcggggggcg gcccgtagcc cagtccgtcg cctgccattg gacgccgccc gctcctcgta    2640
aaggaaaaag ctcggcggag ggcggagtgg tgccttt aaa aggccggcgc cgccttccgc    2700
ctgcaccgcc tcctgcgccg ccccttccga ggctaaatcg cttcctctcg gaacgcgccg    2760 cagaagggt cctggtgacg agtcccgcgt tctctccttg aatccactcg ccagcccgcc    2820
gccctctgcc gccgcaccct gcacacccgc ccctctcctg tgccaggtga gcgcccctct    2880 tgcgggacc cagggaccgt ggagagggtc ttggggggcag tggcgggttg gcgtccgcgt    2940
ggaggcctcc cccattcgcg cccatgccag cgtctcccca ctaccaggca cacacaggct    3000
ccccggcccc tccagcctga ggtcctctaa ctgcgcaatg cagctgcgcg cgctgagtca    3060
tggcggggag gaagccggac gagatgaagg accattctcc ccctttctt gcagggaccc    3120 ctgtggcaaa ggattagggc cccttaccgc tggcgtggat cctaagaggc agtgaggggt    3180
gggggccggc ccatgtacag ccccagggtt ctcgcaagtg ggagcttggt ttctgtcctg    3240
ggaaacgggc gcccttcgcg aggagggaaa cccctcgcgt gcttgatgcc cccttaacac    3300
tttccctgtc tctccttatc gggcgaccat tgattctgag cccggaacag ctgcagccat    3360
gcgaagcgac gggagcattt ttcaggggaa ggcgcttgct cctccacgtt cttgccccgt    3420
aggaacagtg acgatggcaa agcttaccgc tttcctgcct gggctagggc tagttccgcc    3480
gcccttccct gggcttctcc ttgctctctt atattttcc taatgcccct ttcctaccac    3540 ccgcccccctc cttgtgggga aaagcctgac cttgggatgt ccttgaagcc ttggagcccg    3600 ggccagcccct gggatcttga ggggattgga aggaacaccc agtggcagtc agaagagctg    3660
ggttctaacc tcagatctgg ctccggggtt gctgtgtggc ttgaagcaca gaccttttccc    3720 atatctgggc cctttcccac gagggtgttg ggccctctgc ttgattcacg atctttacat    3780
tctaaaatac tccggttcgg ttttgttttc aggcaaggtg accccatggc aaggcgcaag    3840
ccagaagggt ccagcttcaa catgacccac ctgtccatgc tatggccttt tcctttcccc    3900
cagttgccag tggcaactc caccctcagc tgggcaacac ccagcaccag acagagttag    3960
gaaaggtacc ggggcaggcc tagcaaaggg aagttgggcg taagagagag ctggggacca    4020
gaagtgcccc agggcctgct gggtgtgggg caggggaggg agggaacatt tccctgacct    4080
ccaggagagg ggccctggtc atcgggagat gatgggaaac cctagctaac tagtccttcc    4140
cctctgtttc ctgtatccag gaacttgcta ctaccagcac catgccctac caatatccag    4200
cactgacccc ggagcagaag aaggaactgt ctgacatcgc tcaccgcatc gtggcacctg    4260
gcaagggcat cctggctgca gatgagtcca ctggtcgcgg gcaggagaca gaatgggtgg    4320
agggtgcagg gttgggagtg gcaggctgat cccctaattc ccatgtgaca ctcccaggga    4380
gcattgccaa gcgctgcag tccattggca ccgagaacac cgaggagaac cggcgcttct    4440
accgccagct gctgctgaca gctgacgacc gcgtgaaccc cggcattggg ggtgtcatcc    4500
tcttccatga gacactctac cagaaggcgg atgatgggcg tcccttcccc caagttatca    4560
aatccaaggg cggtgttgtg ggcatcaagg taaggggagg gcctccggac gtgaggtttg    4620
```

```
agtaggaagt ggaggaagga aatccaggtt agtgaggcag ggaatgaatg ctggattggt    4680
ggcctagaga cttgcatgga gcctgcttca ggcttagggc atttactcga cattttttat    4740
cctcacaatt ctgagagaac agtatcattc ccactttaca catgaaaatc tcagaagctc    4800
agggaagtga agtgttttgc tcagagtaag tggcagagcc cagtctgaca cccaattcac    4860
tcaacatttc tgttgtcaat aacatcccag tgtatcctgt ctcagaggat tgttactaag    4920
tgaactaagt gaaaatattt taatttaatt gtaactaagt atttgagtaa ctaaacattt    4980
taagtaaatt tttattttt ttttttttga gatggagtct cgctgtctcc caggctggag    5040
tgcagtggtg cgatctcttg ctcactgca agttccgcct cccaggttca cgccattctc    5100
ctgcctcagc ctcccgagta gctgggacta caggcgcccg ccaccacccg gctaattttt    5160
tttgtatttt tagtagacac tgggtttcac catgttagcc aggatggtct cgatctcctg    5220
atctcgtgat ctgcccacct cggcctccct aagtgctggg attacaggcg tgcagccatg    5280
cccggcttaa gtaactaaat attttaattg taactaagtg aaaatatttg ccagccctga    5340
agatgcagtt taagggatta acgtaaaata gtgggggaag actggggcta agaagagga    5400 aagagggca cgccagctac ctaggaggct gaggcgggag gatcacttga gtccaggaag    5460
gggaggcttc aggtgagctg agattccacc actgtactcc agccgaggcg aaagtggaaa    5520
gggtgctaga ggtcatttcc tgtgtcttaa tgttgttacc ctgaccccaa caggtagaca    5580
agggcgtggt cccctggca gggacaaatg gcgagactac cacccaaggt gagaactgtt    5640
tgattctctg ccctacgaac ccaaccagag caggtttggg tgctgggagg agtggaaacc    5700
acatgcccct cccaccctgc tctgaccttc ctcttctctt agggttggat gggctgtctg    5760
agcgctgtgc ccagtacaag aaggacggag ctgacttcgc caagtggcgt tgtgtgctga    5820
agattgggga acacaccccc tcagccctcg ccatcatgga aaatgccaat gttctggccc    5880
gttatgccag tatctgccag caggtggcct gcaggtcctc aataggcaac ctcctacctc    5940
atttggttcc agtgttgtta atttgcctat taactgccat gatgcctacc tccccaaaag    6000
caagcattag cttttggcgcg tggaggcact caagggctgt tgaaggcaga ggggccaagg    6060
agggatggtg ggtggatctg aggcggctct tgtctcctgt aatctagggc tttgaagcct    6120
gagtccctgg catcatcaag atacggtctt gaccagtggc tgtggagaga tgtaggtggg    6180
actctgggtt aggaggcctc acagtgaccc tgtccctcgc cctgcagaat ggcattgtgc    6240
ccatcgtgga gcctgagatc ctccctgatg gggcccatga cttgaagcgc tgccagtatg    6300
tgaccgagaa ggtaaatggc tacctgcctg accagtgcaa ggtggctggc cggggacctt    6360
ggggctaacc cctatcctct cctccacccc actacccacc gtgcgcctgc tctgctcagg    6420
tgctggctgt tgtctacaag gctctgagtg accaccacat ctacctggaa ggcaccttgc    6480
tgaatcccaa catggtcacc ccaggccatg cttgcactca gaagttttca catgaggaga    6540
ttgccatggc gaccgtcaca cgcgctgcgcc gcacagtgcc ccccgctgtc actggtgagg    6600
cccactcatc ttgatctcta tgcagtagat aagctccacc cacaacccta tgcccatttg    6660
gacggatttc ccatggcaac ttccaccagc tcctgccagc ttcctgggtc tctgacacag    6720
ccccctctgc tacccctgc actacaggga tcaccttcct gtctggaggc cagagtgagg    6780
aggagtcgtc catcaacctc aatgccatta acaagtgccc cctgctgaag ccctgggccc    6840
tgaccttctc ctacggccga gccctgcagg cctctgccct gaaggcctgg ggcgggaaga    6900
aggagaacct gaaggctgcg caggaggagt atgtcaagcg agcccggta aggataggca    6960 ggaggtgggc agggtgcctg ggtggatggg actcgggaa gagcccttct cactccaccc    7020
```

```
ctctccctgc ttaggccaac agccttgcct gtcaaggaaa gtacactccg agcggtcagg    7080
ctggggctgc tgccagcgag tccctcttcg tctctaacca cgcctattaa gcggaggtgt    7140
tcccaggctg cccccaacac tccaggccct gcccctccc  actcttgaag aggaggccgc    7200
ctcctggggc tccaggctgg cttgccgcgc tctttcttcc ctcgtgacag tgttgtgtgg    7260
tgtcgtctgt gaatgctaag tccatcaccc tttccgggac actgccaaat aaacagctat    7320
ttaaggggga gtcggccgtc cgtgtcttgt ggtgtctaat gcaggggagg gcctggggag    7380
gtagcagagc ccagaagaag aaagagcccc tgttctctgt ttttctggg  cagaaaagga    7440 gtgaaaggtg gaaggacctt cctgctctgt tttatacttg gccagggctt caagaaaggc    7500
tgagagctgt gacattttct tcactgcagg                                     7530
```

<210> SEQ ID NO 4
<211> LENGTH: 1092
<212> TYPE: DNA
<213> ORGANISM: Homo sapiens

<400> SEQUENCE: 4

```
atgccctacc aatatccagc actgaccccg gagcagaaga aggagctgtc tgacatcgct     60
caccgcatcg tggcacctgg caagggcatc ctggctgcag atgagtccac tgggagcatt    120
gccaagcggc tgcagtccat ggcaccgag  aacaccgagg agaaccggcg cttctaccgc    180
cagctgctgc tgacagctga cgaccgcgtg aacccctgca ttgggggtgt catcctcttc    240
catgagacac tctaccagaa ggcggatgat gggcgtccct cccccaagt  tatcaaatcc    300 aagggcggtg ttgtgggcat caaggtagac aagggcgtgg tcccctggc  agggacaaat    360 ggcgagacta ccacccaagg gttggatggg ctgtctgagc gctgtgccca gtacaagaag    420
gacggagctg acttcgccaa gtggcgttgt gtgctgaaga ttggggaaca caccccctca    480
gccctcgcca tcatggaaaa tgccaatgtt ctggcccgtt atgccagtat ctgccagcgg    540
aatggcattg tgcccatcgt ggagcctgag atcctccctg atgggaccca tgacttgaag    600
cgctgccagt atgtgaccga aaggtgctg  gctgctgtct acaaggctct gagtgaccac    660
cacatctacc tggaaggcac cttgctgaag cccaacatgg tcaccccagg ccatgcttgc    720
actcagaagt tttctcatga ggagattgcc atggcgaccg tcacagcgct gcgccgcaca    780
gtgccccccg ctgtcactgg gatcaccttc ctgtctggag ccagagtga  ggaggaggcg    840 tccatcaacc tcaatgccat taacaagtgc ccctgctga  agccctgggc cctgaccttc    900
tcctacggcc gagccctgca ggcctctgcc ctgaaggcc  ggggcgggaa gaaggagaac    960
ctgaaggctg cgcaggagga gtatgtcaag cgagccctgg ccaacagcct tgcctgtcaa   1020
ggaaagtaca ctccgagcgg tcaggctggg gctgctgcca gcgagtccct cttcgtctct   1080
aaccacgcct at                                                       1092
```

<210> SEQ ID NO 5
<211> LENGTH: 1499
<212> TYPE: DNA
<213> ORGANISM: Homo sapiens

<400> SEQUENCE: 5

```
cgccgcccct tccgaggcta atcggctgc  gttcctctcg gaacgcgccg cagaagggt      60 cctggtgacg agtcccgcgt tctctccttg aatccactcg ccagcccgcc gccctctgcc    120
gccgcaccct gcacacccgc ccctctcctg tgccaggaac ttgctactac cagcaccatg    180
ccctaccaat atccagcact gaccccggag cagaagaagg agctgtctga catcgctcac    240
```

| | | |
|---|---|---|
| cgcatcgtgg cacctggcaa gggcatcctg ctgcagatg agtccactgg gagcattgcc | 300 | |
| aagcggctgc agtccattgg caccgagaac accgaggaga accggcgctt ctaccgccag | 360 | |
| ctgctgctga cagctgacga ccgcgtgaac ccctgcattg ggggtgtcat cctcttccat | 420 | |
| gagacactct accagaaggc ggatgatggg cgtcccttcc cccaagttat caaatccaag | 480 | |
| ggcggtgttg tgggcatcaa ggtagacaag ggcgtggtcc ccctggcagg gacaaatggc | 540 | |
| gagactacca cccaagggtt ggatgggctg tctgagcgct gtgcccagta caagaaggac | 600 | |
| ggagctgact tcgccaagtg gcgttgtgtg ctgaagattg ggaacacac cccctcagcc | 660 | |
| ctcgccatca tggaaaatgc caatgttctg gcccgttatg ccagtatctg ccagcagaat | 720 | |
| ggcattgtgc ccatcgtgga gcctgagatc ctccctgatg ggaccatga cttgaagcgc | 780 | |
| tgccagtatg tgaccgagaa ggtgctggct gctgtctaca aggctctgag tgaccaccac | 840 | |
| atctacctgg aaggcacctt gctgaagccc aacatggtca ccccaggcca tgcttgcact | 900 | |
| cagaagtttt ctcatgagga gattgccatg gcgaccgtca cagcgctgcg ccgcacagtg | 960 | |
| ccccccgctg tcactgggat caccttcctg tctggaggcc agagtgagga ggaggcgtcc | 1020 | |
| atcaacctca tgccattaa caagtgcccc ctgctgaagc cctgggccct gaccttctcc | 1080 | |
| tacggccgag ccctgcaggc ctctgccctg aaggcctggg cgggaagaa ggagaacctg | 1140 | |
| aaggctgcgc aggaggagta tgtcaagcga gccctggtaa ggataggcag gaggtgggca | 1200 | |
| gggtgcctgg gtggatggga ctcggagaag agcccttctc actccacccc tctccctgct | 1260 | |
| taggccaaca gccttgcctg tcaaggaaag tacactccga gcggtcaggc tggggctgct | 1320 | |
| gccagcgagt ccctcttcgt tctaaccac gcctattaag cggaggtgtt cccaggctgc | 1380 | |
| ccccaacact ccaggccctg cccccttccca ctcttgaaga ggaggccgcc tcctcggggc | 1440 | |
| tccaggctgg cttgcccgcg ctctttcttc cctcgtgaca gtggtgtgtg gtgtcgtct | 1499 | |

<210> SEQ ID NO 6
<211> LENGTH: 1669
<212> TYPE: DNA
<213> ORGANISM: Homo sapiens

<400> SEQUENCE: 6

| | | |
|---|---|---|
| aaaaacatga tgagaagtct ataaaaattg tgtgctacca aagatctgtc ttatttggca | 60 | |
| gctgctgcct cacccacagc ttttgatatc taggaggact cttctctccc aaactacctg | 120 | |
| tcaccatggc ccaccgattt ccagccctca cccaggagca aagaaggag ctctcagaaa | 180 | |
| ttgcccagag cattgttgcc aatggaaagg ggatcctggc tgcagatgaa tctgtaggta | 240 | |
| ccatggggaa ccgcctgcag aggatcaagg tggaaaacac tgaagagaac cgccggcagt | 300 | |
| tccgagaaat cctcttctct gtggacagtt ccatcaacca gagcatcggg ggtgtgatcc | 360 | |
| ttttccacga ccctctac cagaaggaca gccagggaaa gctgttcaga aacatcctca | 420 | |
| aggaaagggg gatcgtggtg ggaatcaagt tagaccaagg aggtgctcct cttgcaggaa | 480 | |
| caaacaaaga aaccaccatt caagggcttg atggcctctc agagcgctgt gctcagtaca | 540 | |
| agaaagatgg tgttgacttt gggaagtggc gtgctgtgct gaggattgcc gaccagtgtc | 600 | |
| catccagcct cgctatccag gaaaacgcca acgccctggc tcgctacgcc agcatctgtc | 660 | |
| agcagaatga actggtacct attgttgaac cagaggtaat tcctgatgga gaccatgacc | 720 | |
| tggaacactg ccagtatgtt actgagaagg tcctggctgc tgtctacaag gccctgaatg | 780 | |
| accatcatgt ttacctggag ggcacccctgc taaagcccaa catggtgact gctggacatg | 840 | |
| cctgcaccaa gaagtatact ccagaacaag tagctatggc caccgtaaca gctctccacc | 900 | |

-continued

```
gtactgttcc tgcagctgtt cctggcatct gcttttgtc tggtggcatg agtgaagagg    960
atgccactct caacctcaat gctatcaacc tttgccctct accaaagccc tggaaactaa   1020
gtttctctta tggacgggcc ctgcaggcca gtgcactggc tgcctggggt ggcaaggctg   1080
caaacaagga ggcaacccag gaggctttta tgaagcgggc catggctaac tgccaggcgg   1140
ccaaaggaca gtatgttcac acgggttctt ctggggctgc ttccacccag tcgctcttca   1200
cagcctgcta tacctactag ggtccaatgc ccgccagcct agctccagtg cttctagtag   1260
gagggctgaa agggagcaac ttttcctcca atcctggaaa ttcgacacaa ttagatttga   1320
actgctggaa atacaacaca tgttaaatct aagtacaag ggggaaaaaa taaatcagtt    1380
attgaaacat aaaaatgaat accaaggacc tgatcaaatt tcacacagca gtttccttgc   1440
aacactttca gctccccatg ctccagaata cccacccaag aaaataatag ctttaaaac    1500
aatatcggct cctcatccaa agaacaactg ctgattgaaa cacctcatta gctgagtgta   1560
gagaagtgca tcttatgaaa cagtcttagc agtggtaggt tgggaaggag atagctgcaa   1620
ccaaaaaaga aataaatatt ctataaacct tcaaaaaaaa aaaaaaaa                 1669

<210> SEQ ID NO 7
<211> LENGTH: 4656
<212> TYPE: DNA
<213> ORGANISM: Homo sapiens

<400> SEQUENCE: 7
ggccagttta gttgtgctca gtggctatgg attgcaacac attggtctaa tgaggcctgg     60
agattggttc agaagctttt gccaagcaac aaataagaat tccttcatcc tgcctccctg    120
cagtgtaaat gtgccaaggt caagtggctc tatgactagc tttgagtttc acctggtggg    180
acctcttgtc cttcaggtcc tcgctgctgt ctacaaggcc ctgaatgacc atcatgttta    240
cctggagggc accctgctaa agcccaacat ggtgactgct ggacatgcct gcaccaagaa    300
gtatactcca gaacaagtag ctatggccac cgtaacagct ctccaccgta ctgttcctgc    360
agctgttcct ggtaaggcct tctttcttct ctaactcaag gtcttagccc tcattctttg    420
gagagccaca agctttctgt ttgtccagaa atctgcttct attcatgaaa caaacctctg    480
ttatctcaca ggcagccagc acttcttctc ccacttcaga ataccaagca tcccaagtct    540
gcccaaatgc ccacaatcca tgtatttctt caacatttca ctgccttcct tacgtattta    600
aagcacttat ctctagccca actagcttca gcaaaagcaa actgatttct cagtttgctt    660
taaggcaaat taagcagaga aaagactgag acattacttt tctggtaggt tcattgcttg    720
ctttctcaag cagggtatat aaggtgggac taatagagtg aaatggcctt ctctcctacc    780
aggcatctgc tttttgtctg gtggcatgag tgaagaggat gccactctca acctcaatgc    840
tatcaacctt tgccctctac caaagccctg gaaactaagt ttctcttatg gacgggccct    900
gcaggccagt gcactggctg cctggggtgg caaggctgca acaaggagg caacccagga    960
ggcttttatg aagcgggcca tggtaagatg ctgccacctc ttatctactt gatgatgttc   1020
acatttgggg cttgactttc aacacggag aagcattgtt ttcttcggc caagaaggta    1080
tctaccaata gtgtctatta ggcatttgaa aatgtggcag tagaggtcag tatgaggatt   1140
gaggctagag agaattttga attatccaca ctagagtata gttgatgaca ggagactgaa   1200
ggacaatttc aacagaaaca cttcagaggg aaggagataa gaggaccaag aactgaacct   1260
aggatacttt ttatttttggg aagatgaaga agagaagcaa ccaagaaaag cagcgattat   1320
attgtagggt gaaccaagca ttctgggaat aaagacagaa gaatttctttt ctttcatgtt   1380
```

```
tatttgtttg tttgtttgtt tgttttgaga tggagtgtta ctctgtcacc caggctggag    1440
tacagtggca caatctcggc tcactgcaac ctccacctcc tggattcaag caattcttct    1500
gcctcagcct cccaagtagc tgggactaga ggcatgcgcc accatacctg gctaatttct    1560
gtatatttta gtaaagatgg ggtttcacca tgttggccag gctggtctca aactcctgac    1620
ctcaggtgat ctgcccacct caacctccca aagtgctgag attacagaca tgagccacca    1680
caccagccgg gtaaacaatt tcaaagggcc aataataaca tgctatagag agattcaaaa    1740
gaaaggccaa gaaaagaccc tgagattggc atttaggagc ataccagtga ccctcactga    1800
aacagtttca ataagagga aaggaaaggt gcccactcaa gaagttttc agaaaaagac    1860 ccagaaaggt tgccaggaga atgaggacc aacaaagttt ttattcaaat aataaccaaa    1920 attttaaaa tacgctttat gagccaagaa ctggggtgaa caaatgagac atagccatgt    1980
cctccaggaa gcttggagtt tagccaaata ggagagagct tggcatgttt aaatgtaaag    2040
aaagaggagc cagaggagac agtaaagatg aggagagtgg ggataattga gtggagaaga    2100
acttagagga gcaggactgc atgagactca atattaagca taggtggcac agctggtgta    2160
agacaaaaag gagggaagag gcagaaaaga gaatacagtt ggaatcagct ctatataagt    2220
caagagatgt agcagttgat gactgattac agttgagggt atctgctgag aatgatgaag    2280
aaatggaaat ttcaatactg acagtcggaa agcgtagaaa agcagttaaa ggaacttgct    2340
aggaaattga tcggacgtta tggccagaca tagccaagca tcaggtaatg tgcagctgaa    2400
ataagagtga gtgtgtggta gcttcattcc tgagttttcc taacagcagt ctaaagcatg    2460
caggaagatt cagaacgcaa aatagcgggg tagaagagtg aaagtttaat aggaagatag    2520
aagagtgaca aattttaccg atagcctctg ttagcttgct gaccatagag gaagctaggc    2580
aaggaatcaa gagtagtcag aagtgtggtg atgaggccct aaagggaagg aaggccccag    2640
ggaagctaaa tcatcatctc acaggcataa gagaggtatc agattttcaa agtagtgctt    2700
taccttgact gtggaaagca gggtgcagca gtgctgctgt gtggctgatg gactgaggag    2760
acctagctta catgatggag ggattgtgaa agcgcaggtc atcagggaca tccacacaga    2820
agaagggaag ctgagtttat catcaagaat ggtgcttccc aagctccagt gtggatctga    2880
atcacctgaa ggtgattttg gttttgttgt tatgatcttt tatatttaca cacaataatt    2940
gtatagatct gtgggtatc tgtgattttt tatatatgca tataatgtat aatgatcaaa    3000
tcaggataat tagggtattc actccaaata tttattattt ctttgggttt ggaacattcc    3060
aaatcttctc ttccagctat tttaaaatat gtaataaatc attgttaact atagtcatct    3120
tactgttgta tcaaacacta gaacttattc cttctgccta actgtatttt tgtacccatt    3180
accaacctct tttcatttcc cctacccccca cttgaagcgc ttgttaaaaa tgcagattat    3240
gggtctcacc cactgagttt ctaattcagt aggtcagggg taaggccagg gaatttctat    3300
ttttaacatg ttcctaaggg atgctggtag accatgaaac acagttggag aaccattgat    3360
gtaaaatgta gaaataagtc ctggagagaa cagacaatag caacactgac tggaagaagt    3420
ggtaccactg agtgacattc aaatattgtc gtaagtttca taattctgaa tttatcttta    3480
actggaatgt atacaggaaa gcaaatgata ctacaataac taaataaaaa ttacatattc    3540
ttctagacca atataggtag aaaatggaaa tgttttttaaa ataaacatgt ttttctttttg    3600 gtatagtgta ctatactagt gagaaatttt tcaactttag tttctagtac tgttgctgca    3660
atattgttgg tactgaacag agatttcccc agtaactgac acaaacctca agcttaccaa    3720
agaaatgctc agaaaactgg gataaaaagg ggagatactt tatagaaggg gatggtatcc    3780
```

```
ccagcaatat tcagcaacat tgctgtaaaa agaagaaaat ctgagtgaag gtttgactgg      3840
tttcccatga gaggcagaca gggtcaaggt ggggtcacat ttactctaac cagtctcctc      3900
tctcatattt gtcttctagg ctaactgcca ggcggccaaa ggacagtatg ttcacacggg      3960
ttcttctggg gctgcttcca cccagtcgct cttcacagcc tgctatacct actagggtcc      4020
aatgcccgcc agcctagctc cagtgcttct agtaggaggg ctgaaaggga gcaactttc      4080 ctctaatcct ggaaattcga cacaattaga tttgaactgc tggaaataca acacatgtta     4140
aatcttaagt acaaggggga aaaataaat cagttattga aacataaaaa tgaataccaa      4200
ggacctgatc aaatttcaca cagcagtttc cttgcaacac tttcagctcc ccatgctcca     4260
gaatacccac ccaagaaaat aataggcttt aaaacaatat cggctcctca tccaaagaac     4320
aactgctgat tgaaacacct cattagctga gtgtagagaa gtgcatctta tgaaacagtc     4380
ttagcagtgg taggttggga aggagatagc tgcaaccaaa aaagaaataa atattctata    4440
aaccttcagc tgctatcggg tttcactttt ctgctcttgc tgtccaaaga ctcagtgtat    4500
ttcattactt ttgactctac tagacatgac tgggtttcaa cagtaaaggt cttcaactct    4560
tgctagtcat tggaatcaag ccgcaaaatt ttaaaaactg agatgctcag gccacacccc    4620
agctcaatta aatcagaaac cctagacttg ggatcc                              4656

<210> SEQ ID NO 8
<211> LENGTH: 1174
<212> TYPE: DNA
<213> ORGANISM: Homo sapiens

<400> SEQUENCE: 8
aacttatttg gcagctgctg cctcacccac agcttttgat atctaggagg actcttctct       60
cccaaactac ctgtcaccat ggcccaccga tttccagccc tcacccagga gcagaagaag      120
gacagccagg gaaagctgtt cagaaacatc ctcaaggaaa aggggatcgt ggtgggaatc      180
aagttagacc aaggaggtgc tcctcttgca ggaacaaaca aagaaccac cattcaaggg      240 cttgatggcc tctcagagcg ctgtgctcag tacaagaaag atggtgttga ctttgggaag      300
tggtgtgctg tgctgaggat tgccgaccag tgtccatcca gcctcgctat ccaggaaaac      360
gccaacgccc tggctcgcta cgccagcatc tgtcagcaga atggactggt acctattgtt      420
gaaccagagg taattcctga tggagaccat gacctggaac actgccagta tgttactgag      480
aaggtcctgg ctgctgtcta caaggccctg aatgaccatc atgtttacct ggagggcacc      540
ctgctaaagc ccaacatggt gactgctgga catgcctgca ccaagaagta tactccagaa      600
caagtagcta tggccaccgt aacagctctc caccgtactg ttcctgcagc tgttcctggc      660
atctgctttt tgtctggtgg catgagtgaa gaggatgcca ctctcaacct caatgctata      720
cctactaggg tccaatgccc gccagcctag ctccagtgct tctagtagga gggctgaaag      780
ggagcaactt ttcctctaat cctggaaatt cgacacaatt agatttgaac tgctggaaat      840
acaacacatg ttaaatctta agtacaaggg ggagaaaata aatcagttat tgaaacataa      900
aaatgaatac caaggacctg atcaaatttc acacagcagt ttccttgcaa cactttcagc      960
tccccatgct ccagaatacc cacccaagaa aataataggc tttaaaacaa tatcggctcc     1020
tcatccaaag aacaactgct gattgaaaca cctcattagc tgagtgtaga gaagtgcatc     1080
ttatgaaaca gtcttagcag tggtaggttg gaaggagat agctgcaacc aaaaaagaaa     1140
taaatattct ataaaccttc aaaaaaaaaa aaaa                                1174

<210> SEQ ID NO 9
```

```
<211> LENGTH: 1422
<212> TYPE: DNA
<213> ORGANISM: Homo sapiens

<400> SEQUENCE: 9
cttatttggc agctgctgcc tcacccacag cttttgatat ctaggaggac tcttctctcc      60
caaactacct gtcaccatgg cccaccgatt ccagccctc  acccaggagc agaagaagga     120
gctctcagaa attgcccaga gcattgttgc caatggaaag gggatcctgg ctgcagatga     180
atctgtaggt accatgggga accgcctgca gaggatcaag gtggaaaaca ctgaagagaa     240
ccgccggcag ttccgagaaa tcctcttctc tgtggacagt tccatcaacc agagcatcgg     300
gggtgtgatc cttttccacg agaccctcta ccagaaggac agccagggaa agctgttcag     360
aaacatcctc aaggaaaagg ggatcgtggt gggaatcaag ttagaccaag aggtgctcc     420
tcttgcagga acaaacaaag aaaccaccat tcaagggctt gatggcctct cagagcgctg     480
tgctcagtac aagaaagatg gtgttgactt tgggaagtgg cgtgctgtgc tgaggattgc     540
cgaccagtgt ccatccagcc tccctatcca ggaaaacgcc aacgccctgg ctcgctacgc     600
cagcatctgt cagcagaatg gactggtacc tattgttgaa ccagaggtaa ttcctgatgg     660
agaccatgac ctggaacact gccagtatgt tactgagaag gtcctggctg ctgtctacaa     720
ggccctgaat gaccatcatg tttacctgga gggcacctg  ctaaagccca acatggtgac     780
tgctggacat gcctgcacca agaagtatac tccagaacaa gtagctatgg ccaccgtaac     840
agctctccac cgtactgttc ctgcagctgt tcctggcatc tgcttttgt  ctggtggcat     900
gagtgaagag gatgccaccc tcaacctcaa tgctatcaac ctttgccctc taccaaagcc     960
ctggaaacta gtttctctg  ggtggcaag  gctgcaaaca aggaggcaac ccaggaggct    1020
tttatgaagc gggccatggc taactgccag gcggccaaag acagtatgt  tcacgggt     1080
tcttctgggg ctgcttccac ccagtcgctc ttcacagcct gctataccta ctagggtcca    1140
atgcccgcca gcctagctcc agtgcttcta gtaggagggc tgaaagggag caacttttcc    1200
tccaatcctg gaaattcgac acaattagat ttgaactgct ggaaatacaa cacatgttaa    1260
atcttaagta caaggggaa  aaaataaatc agttgttgaa acataaaaat gaataccaag    1320
gacctgatca aatttcacac agcagttttcc ttgcaacact ttcagctccc catgctccag    1380
aatacccacc caaaaaaaaa aaaaaaaaaa aaaaaaaaa aa                        1422

<210> SEQ ID NO 10
<211> LENGTH: 1582
<212> TYPE: DNA
<213> ORGANISM: Homo sapiens

<400> SEQUENCE: 10
ccgagctgtg cttgtggctg cggctgctaa ctggctgcgc acagggagct gtcaccatgc      60
ctcactcgta cccagccctt tctgctgagc agaagaagga gttgtctgac attgccctgc     120
ggattgtagc cccgggcaaa ggcattctgg ctgcggatga gtctgtaggc agcatggcca     180
agcggctgag ccaaattggg gtggaaaaca cagaggagaa ccgccggctg taccgccagg     240
tcctgttcag tgctgatgac cgtgtgaaaa agtgcattgg aggcgtcatt ttcttccatg     300
agaccctcta ccagaaagat gataatggtg ttccccttcgt ccgaaccatc caggataagg     360
gcatcgtcgt gggcatcaag gttgacaagg gtgtggtgcc tctagctggg actgatggag     420
aaaccaccac tcaagggctg gatgggctct cagaacgctg tgcccaatac aagaaggatg     480
gtgctgactt tgccaagtgg cgctgtgtgc tgaaaatcag tgagcgtaca ccctctgcac     540
```

-continued

| | |
|---|---|
| ttgccattct ggagaacgcc aacgtgctgg cccgttatgc cagtatctgc cagcagaatg | 600 |
| gcattgtgcc tattgtggaa cctgaaatat tgcctgatgg agaccacgac ctcaaacgtt | 660 |
| gtcagtatgt tacagagaag gtcttggctg ctgtgtacaa ggccctgagt gaccatcatg | 720 |
| tatacctgga ggggaccctg ctcaagccca acatggtgac cccgggccat gcctgtccca | 780 |
| tcaagtatac cccagaggag attgccatgg caactgtcac tgccctgcgt cgcactgtgc | 840 |
| ccccagctgt cccaggagtg accttcctgt ctggggtca gagcgaagaa gaggcatcat | 900 |
| tcaacctcaa tgccatcaac cgctgccccc ttccccgacc ctgggcgctt accttctcct | 960 |
| atgggcgtgc cctgcaagcc tctgcactca atgcctggcg agggcaacgg gacaatgctg | 1020 |
| gggctgccac tgaggagttc atcaagcggg ctgaggtgaa tgggcttgca gcccagggca | 1080 |
| agtatgaagg cagtggagaa gatggtggag cagcagcaca gtcactctac attgccaacc | 1140 |
| atgcctactg agtatccact ccataccaca gcccttggcc cagccatctg cacccacttt | 1200 |
| tgcttgtagt catggccagg gccaaatagc tatgcagagc agagatgcct tcacctggca | 1260 |
| ccaacttgtc ttcctttctc tcttcccttc ccctctctca ttgctgcacc tgggaccata | 1320 |
| ggatgggagg atagggagcc cctcatgact gagggcagaa gaaattgcta gaagtcagaa | 1380 |
| caggatggct gggtctcccc ctacctcttc cagctccac aattttccca tgatgaggta | 1440 |
| gcttctccct gggctctcct tcttgcctgc cctgtctcct gggatcagag ggtagtacag | 1500 |
| aagccctgac tcatgccttg agtacatacc atacagcaaa taaatggtag caaaacaaaa | 1560 |
| aaaaaaaaaa aaaaaaaaa aa | 1582 |

<210> SEQ ID NO 11
<211> LENGTH: 6694
<212> TYPE: DNA
<213> ORGANISM: Homo sapiens

<400> SEQUENCE: 11

| | |
|---|---|
| aagcttgcat gcaggccacg ccccggagag tcacgtagct ctgcgacatc cgcagcctca | 60 |
| tttaccagag ggagccaggg ctgcagctca tctgtttgcg gatcaagaac ccgagctgtg | 120 |
| cttgtggctg cggctgctaa ctggctgcgc acaggtaagg ccaggcaagg cgggaccgac | 180 |
| tcaacatctt ccgcttcatt tccttggcct cttcccctgc catcctcgtc ctgctacctg | 240 |
| ggactccggg atgtgccctt tcgacccttt cctaacatct ttgctccttt ccgcgtactt | 300 |
| gaaaccccat ggctcaacct cttctgttct atccctcttc agctctccca gctggacctc | 360 |
| agcttttcca atcccaaatc ctcctctact tgttggattt ttccttggag tctgtctctc | 420 |
| ctacccagag catttccttc tcagcctgct ccctctcctc ctaggctagg tcctctctcc | 480 |
| agttctcccg ccttctctgc ccccggtct aggtctctcc cgctgactgg ttagcctgca | 540 |
| tcaccactag ctcccctcag tctcatctct ctctcaggct ctctactcct ttcagccttg | 600 |
| gtcctctgcc ctcccgtctg ggtgtctaga ttgtggggaa ttgaagtgct tcctattgct | 660 |
| atcctcctgc caaacaggtg aagtgcttcc tgggcacaga gatgacccgg aggtgtcact | 720 |
| agccctagtc tccacacact aacacagctg accgctgggc cctctttcc tacatcactg | 780 |
| cagccccact ggggccaacc tctggtactg ggtgggaata ggcaataggc ataggcaggc | 840 |
| aggtttggag tacagaaaag gagaagctgc aggagcctgt gactggtatt tgtgccactc | 900 |
| ctactcccta cctgttcttc caacctttc ctctagaagc tgagagaaga gggtggcaat | 960 |
| aagtactttt gcctcattct gaagccttgg aagtaagtac actttcctag ggtcctgtg | 1020 |
| gaggatgaga aagggaagc tggaaaggcc aggacttttg cctacctcaa caagggacca | 1080 |

```
agttcagtga aagaagggtt ggcatccttg atgggcagc agatttatca gaagagctgt      1140
ggcttcaggg ctgctcacct ccccaccccc accctgcatc tttccccagg gctgggaagg      1200
atgcctacca gggacaaaag gagatgtggg aactggagcc ctaagcttgc tagctgtcag      1260
aaggactggt gccacttgat gcccaggact catgccaagg actgctgccc tgttcccagc      1320
cccttgcttg atggggaggc catttggccc atctggccag gagaggcagc agagggtgag      1380
gtctggctt tttatcttgt ctccactcca gggagctgtc accatgcctc actcgtaccc      1440
agccctttct gctgagcaga agaaggagtt gtctgacatt gccctgcgga ttgtagcccc      1500
gggcaaaggc attctggctg cggatgagtc tgtaggtaag tggacatctg tagccaggta      1560
gggtacaggt ggctagggga ccctggggat gttctcactg cctctctttg tttgcccta      1620
ggcagcatgg ccaagcggct gagccaaatt ggggtggaaa acacagagga gaaccgccgg      1680
ctgtaccgcc aggtcctgtt cagtgctgat gaccgtgtga aaagtgcat tggaggcgtc      1740
attttcttcc atgagaccct ctaccagaaa atgataatg tgttccctt cgtccgaacc      1800
atccaggata agggcatcgt cgtgggcatc aaggtgcagc ccctggccct gctctgaatg      1860
gaagctgggt gtgaaaataa gcttgtgtag gaggggtagc aaggagaatc ctgcctggat      1920
tcaaccctct gcttgtactt cctctacagg ttgacaaggg tgtggtgcct ctagctggga      1980
ctgatgagga aaccaccact caaggtatag gatgggtggg cttgaggacc aaagaggtgt      2040
tagatagttg atgctggtaa aagaggggca gagtaatgag gttggcactg tgcttgcagg      2100
gctggatggg ctctcagaac gctgtgccca atacaagaag gatggtgctg actttgccaa      2160
gtggcgctgt gtgctgaaaa tcagtgagcg tacaccctct gcacttgcca ttctggagaa      2220
cgccaacgtg ctggcccgtt atgccagtat ctgccagcag gtgtgtgtgt gggagggtg      2280
gtgagctagg tgccctgtat gcctggtggg gagagagtca caaggctttc ttcatctccc      2340
ctactgcccc tcccaagcat ctctgctctt gcctgcagaa tggcattgtg cctattgtgg      2400
aacctgaaat attgcctgat ggagaccacg acctcaaacg ttgtcagtat gttacagaga      2460
aggtgagtcc acacctgggc acacaaacat actgcaggga cagctcggca ggagtgtctg      2520
ttccccagaa cccccagctt agatccaggc acactttccc ctagcacttt ttcacttcat      2580
cccggcacag gcctgtgatc tgagcctgta ctgagccctc acagtctgtg cccatctacc      2640
cctacatagg gagcatcgag cagtaaccag tgggggccca dacccttagt aaacctcctc      2700
taatccccac ccaggtcttg gctgctgtgt acaaggccct gagtgaccat catgtatacc      2760
tggaggggac cctgctcaag cccaacatgg tgaccccggg ccatgcctgt cccatcaagt      2820
ataccccaga ggagattgcc atggcaactg tcactgccct gcgtcgcact gtgcccccag      2880
ctgtcccagg tactacccag ctccctaacc tgctcctatc cctaaggccc atcttcaggt      2940
ccttcttgtg gccttcaggg gttccctatc ctggaaaaat tgggagtgac cagtcagttt      3000
gtcttctctc ctccacacta ggagtgacct tcctgtctgg gggtcagagc gaagaagagg      3060
catcattcaa cctcaatgcc atcaaccgct gccccttcc ccgaccctgg gcgcttacct      3120
tctcctatgg gcgtgccctg caagcctctg cactcaatgc ctggcgaggg caacgggaca      3180
atgctgggc tgccactgag gagttcatca agcgggctga ggttgggagc tacaggtggt      3240
ggtgggtggg ggcagcaccc agaggctata gcctgggcag gcttggcac ctgtgggctg      3300
gctcagcctg cttactccac gctcccttt gcaggtgaat gggcttgcag cccagggcaa      3360
gtatgaaggc agtggagaag atggtggagc agcagcacag tcactctaca ttgccaacca      3420
tgcctactga gtatccactc cataccacag cccttggccc agccatctgc acccacttt      3480
```

-continued

| | |
|---|---|
| gcttgtagtc atggccaggg ccaaatagct atgcagagca gagatgcctt cacctggcac | 3540 |
| caacttgtct tcctttctct cttcccttcc cctctctcat tgctgcacct gggaccatag | 3600 |
| gatgggagga tagggagccc ctcatgactg agggcagaag aaattgctag aagtcagaac | 3660 |
| aggatggctg ggtctccccc tacctcttcc agctcccaca attttcccat gatgaggtag | 3720 |
| cttctccctg ggctctcctt cttgcctgcc ctgtctcctg ggatcagagg gtagtacaga | 3780 |
| agccctgact catgccttga gtacatacca tacagcaaat aaatggtagc aaaacattct | 3840 |
| actttgcctg tctgttttac acatcaaatt cccacctccc agtttctgat ctctgctaat | 3900 |
| tctatctctg ggccctctga ctctggaggt ggagagggtg ggatttgagt cttactgggc | 3960 |
| ttcaagttat ggaggaaggg cacatgcagt caccatcccc agctcaggct cttgctctct | 4020 |
| tgatgtccaa gtctggagtg gggcaatgag gaagactgca agtcttctag ggactcgcac | 4080 |
| atcagtggca ctgggctgca gctacagaag tatggagtga ggccaaactg gcaactcctg | 4140 |
| aaggcagatt tgtgcaaggc tcaaagcagg gaggcagcaa gacaggctgg gataagagtg | 4200 |
| ggtgggagtc tctcccatct cgcagtgtta agcccagctg ggacctggta ccgcccagct | 4260 |
| gggacctggt accttccact agggtgagcc acaccagtaa gggcaagcga gcacctggac | 4320 |
| tcccgcccaa agaggaaaac caaggctctg cgggctgcca gggctgagca gggcatctag | 4380 |
| gaggttgcca agggctatgg ccattttcat ttggggtaga agtgggcaca aaggagcca | 4440 |
| attggagggt ctgggtaagg acagctctgg tgaggcctga tgctgaactt tgaccactgg | 4500 |
| gctgggttgt gaggtaggct gagaacctgg gtctaagcag ataaaaagaa gagataacaa | 4560 |
| gctgcgtgtg ttctgtgtca actggggagg ctacaaatgc tccaccctgt gtggcctgac | 4620 |
| tttataataa caaaaatagc ttgcacatag caccaacccct gttctaatca ctttatatgt | 4680 |
| actgacacat ttcatacaac tctataaagt aggtactatt actatcatcc ctattttaat | 4740 |
| agagaaaaca ggcacagata ggcacagaac gatcttctca cgatcactca cctaataagt | 4800 |
| gatgaagcca ggatttgaac cgcagtgatc agcatctaga gtctgggctc atgactttc | 4860 |
| aagattttta agtgaagtat tctgagtttt ccaagttgga aatgaattaa aacgtatttt | 4920 |
| aaaatagcga gagaggccaa ttgtgctaaa acatactagc ttgctacctc cgtgtttgag | 4980 |
| gctttgagga gagggcaccc taagaggagt tctacgataa ggataataag accgtgacag | 5040 |
| ttgacgttga gggcttttccg tgtgccaggc tccttacaag aacggcctca tttatgtaaa | 5100 |
| tatctccatt ttcagatgag cctcggagct gcctgtagtt gcccagctag tatttaagga | 5160 |
| ctgcagaggt tgcgctcttg attgcggggc tagaagtgtg ttctacaggg aagcggggaa | 5220 |
| cttcgttcca gcagcgccga aacccgcacg gccctaggc tgtccctccg cgcccgggtg | 5280 |
| acttcctttc agatccccag cgaagctccc agcggagccc tcccacccct cgcccgcttg | 5340 |
| ctcccgtctg cgggtctgga gtagcgctcg cgattggccc cgatcaccgc cgcggtcctg | 5400 |
| cccctcgtt gcagagattc cgattgggtg aggctcacga agctctgccc ccacggtggc | 5460 |
| cggagcagcc ggaagctagc atggcggccg ccggggctgc ggctacacac ctaggtgcgg | 5520 |
| tgggcttcgg gtgggggcc tgcagctagc tgatggcaag ggaggaatag cagggtgggg | 5580 |
| gattgtggtg tgcgagaggt cccgcggacg gggggctcgg gggtctcttc agacgagatt | 5640 |
| cccttcaggc ttgggccggg tcccttcgca cggagatccc aatgaacgcg ggcccctgga | 5700 |
| ggccggtggt tggggcttct ccgcgtcggg gatggggccg gtaccctagc ccgtttccag | 5760 |
| cgcctcagtc ggttccccat gccctcagag gtgcccggg gcaagcgcgc cgccctcttc | 5820 |
| ttcgctgcgg tggccatcgt gctggggcta ccgctctggt ggaagaccac ggagacctac | 5880 |

```
cgggcctcgt tgccttactc ccagatcagt ggcctgaatg cccttcaggt gagactgctg      5940
tgcgggaggg tcgggggaca gccccccccgg caaggtggag actcagtgac ggccctgatg      6000
ctccttcctg tagctccgcc tcatggtgcc tgtcactgtc gtgtttacgc gggagtcagt      6060
gcccctggac gaccaggaga agctgccctt accgttgtgc atgaaagaga gattcctctg      6120
aaatgtgagt tactggggat cagggctgct tttcgcctct gagctcagtt cagagctgag      6180
ttgggtggga ggagcggggg tgtaccataa acgcagttaa aaacttactg ttgaaagacc      6240
tctgaatgaa cagtgtgttt ggtcagaaaa aaaactactt tcaattcaca gtcactaaat      6300
agcaatttta ctcgtaagac aggctaccta atcggaagca gttgatgccc atcagggtat      6360
aggggaagag gtgggatata gtggaaagaa cacagagttt gaaattaaat tggatttgca      6420
tataggccct atttagtttg tttgtttatt tatttattat attttgagac gacttcgctc      6480
tgtcgcccag gctggagtgc agtggcgcca tcttggctca ctgcaacctc tgcctcctgg      6540
gttcaagcga ttcttctgca ccagccaccc gagtagctgg gattacaggc gcgcgacact      6600
acgcccagct aattttttgta ttttttagtag agacggggtt atgccatgtt ggccatgctg      6660
ctctcgaact cctgacttca ggtgatccgc atgc      6694

<210> SEQ ID NO 12
<211> LENGTH: 5198
<212> TYPE: DNA
<213> ORGANISM: Homo sapiens

<400> SEQUENCE: 12
tctagagaaa tatcctagag gagaaccttc ggcgcctctg acaaggagtt agaaaaacta       60
gatgacattg ttcagcatat ttataaggta taggcaggag ggaggtgata tcactaatga      120
acctggtaca aggcctggcc ccaggaggta ctaatgagca cagatctggt tcccagcctg      180
tgctgaagag ctgggcctga atcactattg caggcttctc tgtggtgtct gttttctccc      240
ctctaattca gcggctgcct cctggtggga gccctgggcc ttaagtctgt ggtcctgagc      300
tgcagttttc tgcctctctt cccagccctg ctctctattc cagaggtggt gaggggattg      360
caaagaacta cagggattgc tggaatttct gagctaagaa actgaaagcc agaatctgct      420
tcacctcttt ttacctgcaa taccccctta ccccaatacc aagaccaact ggcatagagc      480
caactgagat aaatgctatt taaataaagt gtatttaatg aatttctcca agcttacgga      540
atcttacttt ttgggtgaga ggggggcgga tgatgaagtc agggaagaag caggcttgtg      600
cctcctgcct gggcacccctc catagatccc tctccacctc ctctgcatcc aaagcaggct      660
gcctgccctt cctcccttcc tcgtactttc accaaaaact ctgggcactg gacgtacttg      720
ttccctcgtc cgcctggagg aaacagaaag cttcattctc tactttcccc agcctcgggg      780
tataccctgg caaatatggg gtgaggacag agaaggctca ggttcattac ttcctgccct      840
gaacttgggc accttgaaga tgcttctgcc ccacctact caacctgttg ttactgttct      900
ggtgcctcct cttcaccaga ctaagcttaa tccccagcat ccagcaagtg cccggcacgt      960
ggtaaaggga ttgtggcaga aatgaacgca aggtcatggc caggctcccc gaggtgggag     1020
ggcagtccct aacagccacg gatgcctggg cgctcactcc acctcgccgc cgcctctgag     1080
ggcgtggtct tgccccggac accagtcctg ggaggggggt gtggtcaggg cgggcatgca     1140
gccacgcccc cggaggagtc acgtagctct gcgacatccg cagcctcatt taccagaggg     1200
agccagggct gcagcctcat ctgtttgcgg atcagaaccc gagctgtgct tgtggctgcg     1260
gctgctaact ggctgcgcac aggtaaggcc aggcaaggcg ggagccactc aacatctccg     1320
```

```
cttcatttcc ttggctcttc ccctgccatc ctcgtcctgc tacctgggac tccgggatgt   1380
gccctttcga ccctttccta acatctttgc tcctttccgc gtacttgaaa ccccatggct   1440
caacctcttc tgttctatcc ctcttcagct ctcccagctg aacctcagct ttccaatccc   1500
aaatcctcct ctacttgttg gattttcct tggagtctgt ctctcctacc cagagcattt    1560
ccttctcagc ctgctccctc tcctcctagg ctaggtcctc tctccagttc tcccgccttc   1620
tctgcccccc ggtctaggtc tctcccgctg actggttagc ctgcatcacc actagctccc   1680
ctcagtctca tctctctctc aggctctcta ctcctttcag ccttggtcct ctgccctccc   1740
gtctggtgtc tatttgggga attaatcttc ctattgctat cctcctgcca aacagctaag   1800
tgcttcctgg cacagagata cccggagtgt cactagccct atctccacac actaacacag   1860
ctgaccgctg ggccctcttt cctacatcac tgcacgactg gggccaacct ctggtactgg   1920
gtgggaatag gcaataggca taggcaggca ggtttgagta cagaaaagaa gctgcaggag   1980
cctgtgactg gtatttgtgc cactcctact ccctacctgt tcttccaacc ttttcctcta   2040
gaagctgaga gaagagggtg gcaataagta cttttgcctc attctgaagc cttggaagta   2100
agtacacttt ccctaggggt cctgtggagg atgagaaaag ggaagctgga aaggccagga   2160
cttttgccta ctcaacaagg gaccaagttc agtgaaagaa gggttggcat ccttgattgg   2220
gcagcagatt tatcagaaga gctgtggctt cagggctgct cacctcccca ccccaccct    2280 gcatctttcc ccagggctgg gaaggatgcc taccagggac aaaaggagat gtgggaactg   2340
gagccctaag cttgctagct gtcagaagga cctggtgcca cttgatgccc aggactcatg   2400
ccaaggactg ctgccctgtt cccagcccct tgcttgatgg ggaggccatt tggcccatct   2460
ggcaggagag gcagcagagg gtgaggtctg gcttttttat cttgtctcca ctccagggag   2520
ctgtcaccat gcctcactcg tacccagccc tttctgctga gcagaagaag gagttgtctg   2580
acattgccct gcggattgta gccccgggca aaggcattct ggctgcggat gagtctgtag   2640
gtaagtggac atctgtagcc aggtagggta caggtggcta ggggaccctg gggatgttct   2700
cactgcctct ctttgtttgc ccctaggcag catggccaag cggctgagcc aaattggggt   2760
ggaaaacaca gaggagaacc gccggctgta ccgccaggtc ctgttcagtg ctgatgaccg   2820
tgtgaaaaag tgcattggag gcgtcatttt cttccatgag accctctacc agaaagatga   2880
taatggtgtt cccttcgtcc gaaccatcca ggataagggc atcgtcgtgg gcatcaaggt   2940
gcagcccctg gccctgctct gaatggaagc tgggtgtgaa aataagcttg tgtaggaggg   3000
gtagcaagga gaatcctgcc tggattcaac cctctgcttg tacttcctct acaggttgac   3060
aagggtgtgg tgcctctagc tgggactgat ggagaaacca ccactcaagg tataggatgg   3120
gtgggcttga ggaccaaaga ggtgttagat agttgatgct ggtaaaagag gggcagagta   3180
atgaggttgg cactgtgctt gcagggctgg atgggctctc agaacgctgt gcccaataca   3240
agaaggatgc tgctgacttt gccaagtggc gctgtgtgct gaaaatcagt gagcgtacac   3300
cctctgcact tgccattctg gagaacgcca acgtgctggc ccgttatgcc agtatctgcc   3360
agcaggtgtg tgtgttggga gggtggtgag ctaggtgccc tgtatgcctg gtggggagag   3420
agtacaaggc tttcttcatc tcccctactg cccctcccaa gcatctctgc tcttgcctgc   3480
agaatggcat tgtgcctatt gtggaacctg aaatattgcc tgatggagac cacgacctca   3540
aacgttgtca gtatgttaca gagaaggtga gtccacacct gggcacacaa acatactgca   3600
gggacagctc ggcaggagtg tctgttcccc agaaccccca gcttagatcc aggcacactt   3660
tcccctagca tttttcactt catcccgcgc acaggcctgg tgatctcgag cctgtactag   3720
```

```
cccctacagtc tgtgcccatc taccccotaca tagggagcat cgagcagtaa ccagtgggg       3780 cccagaccct tagtaaacct cctctaatcc ccacccaggt cttggctgct gtgtacaagg       3840
ccctgagtga ccatcatgta tacctggagg ggaccctgct caagcccaac atggtgaccc       3900
cgggccatgc ctgtcccatc aagtatacco cagaggagat tgccatggca actgtcactg       3960
ccctgcgtcg cactgtgccc ccagctgtcc caggtactac ccagctccct aacctgctcc       4020
tatccctaag gccatcttc aggtccttct tgtggcctta gggggttccc tatcctggaa        4080
aaattgggag tgaccagtca gtttgtcttc tctcctccac actaggagtg accttcctgt       4140 ctggggtca gagcgaagaa gaggcatcat tcaacctcaa tgccatcaac cgctgccccc        4200
ttccccgacc ctgggcgctt accttctcct atgggcgtgc cctgcaagcc tctgcagtca      4260
atgcctggcg agggcaacgg gacaatgctg gggctgccac tgaggagttc atcaagcggg       4320
ctgaggttgg gagctacagg tggtggtggg tgggggcagc accagaggct atagctgggc       4380
agggcttggc agctgtgggc tggctactgc ttactccagg ctcccttttg caggtgaatg       4440
ggcttgcagc ccagggcaag tatgaaggca gtggagaaga tggtggagca gcagcacagt       4500
cactctacat tgccaaccat gcctactgag tatccactcc ataccacagc ccttggccca       4560
gccatctgca cccactttg cttgtagtca tggccagggc caaatagcta tgcaggagca       4620
gagatgcctt cactgcacc aacttgtctt tcctttctct cttcccttcc cctctctcat       4680
tgctgcacct gagaccatag gatgggagga tagggagccc ctcatgactg agggcagaag       4740
aaattgctag aagtcagaac aggatggctg ggtctccccc tacctcttcc agctcccaca       4800
attttcccat gatgaggtag cttctccctg ggctctcctt cttgcctgcc ctgtctcctg       4860
ggatcagagg gtagtacaga agccctgact catgccttga gtacatacca tacagcaaat       4920
aaatggtagc aaaacattct actttgcctg tctgttttac acatcaaatt ccagcctccc       4980
agtttctgat ctctgctaat tctatctctg ggccctctga ctctggaggt ggagagggtg       5040
ggatttgagt cttactgggc ttcaagttat ggaggaaggg caatgcagtc accatcccca       5100
gctcaggctc ttgctctctt gatgtccaag tctggagtgg ggcaatgagg aagactgcaa       5160
gtcttctagg gactgccaca tcagtcgatg ggctgcag                              5198
```

<210> SEQ ID NO 13
<211> LENGTH: 364
<212> TYPE: PRT
<213> ORGANISM: Homo sapiens

<400> SEQUENCE: 13

```
Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
```

```
                 115                 120                 125
Asp Gly Leu Ser Glu Arg Cys Ala Gln Tyr Lys Lys Asp Gly Ala Asp
130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
210                 215                 220

Glu Gly Thr Leu Leu Lys Pro Asn Met Val Thr Pro Gly His Ala Cys
225                 230                 235                 240

Thr Gln Lys Phe Ser His Glu Glu Ile Ala Met Ala Thr Val Thr Ala
                245                 250                 255

Leu Arg Arg Thr Val Pro Pro Ala Val Thr Gly Ile Thr Phe Leu Ser
            260                 265                 270

Gly Gly Gln Ser Glu Glu Ala Ser Ile Asn Leu Asn Ala Ile Asn
        275                 280                 285

Lys Cys Pro Leu Leu Lys Pro Trp Ala Leu Thr Phe Ser Tyr Gly Arg
        290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
            340                 345                 350

Ala Ser Glu Ser Leu Phe Val Ser Asn His Ala Tyr
        355                 360

<210> SEQ ID NO 14
<211> LENGTH: 364
<212> TYPE: PRT
<213> ORGANISM: Homo sapiens

<400> SEQUENCE: 14

Met Ala His Arg Phe Pro Ala Leu Thr Gln Glu Gln Lys Lys Glu Leu
1               5                   10                  15

Ser Glu Ile Ala Gln Ser Ile Val Ala Asn Gly Lys Gly Ile Leu Ala
                20                  25                  30

Ala Asp Glu Ser Val Gly Thr Met Gly Asn Arg Leu Gln Arg Ile Lys
            35                  40                  45

Val Glu Asn Thr Glu Glu Asn Arg Arg Gln Phe Arg Glu Ile Leu Phe
50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
```

-continued

```
                130                 135                 140
Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
                180                 185                 190

Pro Asp Gly Asp His Asp Leu Glu His Cys Gln Tyr Val Thr Glu Lys
                195                 200                 205

Val Leu Ala Ala Val Tyr Lys Ala Leu Asn Asp His His Val Tyr Leu
210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
                260                 265                 270

Gly Gly Met Ser Glu Glu Asp Ala Thr Leu Asn Leu Asn Ala Ile Asn
                275                 280                 285

Leu Cys Pro Leu Pro Lys Pro Trp Lys Leu Ser Phe Ser Tyr Gly Arg
290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335

Gln Ala Ala Lys Gly Gln Tyr Val His Thr Gly Ser Ser Gly Ala Ala
                340                 345                 350

Ser Thr Gln Ser Leu Phe Thr Ala Cys Tyr Thr Tyr
                355                 360
```

<210> SEQ ID NO 15
<211> LENGTH: 364
<212> TYPE: PRT
<213> ORGANISM: Homo sapiens

<400> SEQUENCE: 15

```
Met Pro His Ser Tyr Pro Ala Leu Ser Ala Glu Gln Lys Lys Glu Leu
1               5                   10                  15

Ser Asp Ile Ala Leu Arg Ile Val Ala Pro Gly Lys Gly Ile Leu Ala
                20                  25                  30

Ala Asp Glu Ser Val Gly Ser Met Ala Lys Arg Leu Ser Gln Ile Gly
                35                  40                  45

Val Glu Asn Thr Glu Glu Asn Arg Arg Leu Tyr Arg Gln Val Leu Phe
                50                  55                  60

Ser Ala Asp Asp Arg Val Lys Lys Cys Ile Gly Gly Val Ile Phe Phe
65                  70                  75                  80

His Glu Thr Leu Tyr Gln Lys Asp Asp Asn Gly Val Pro Phe Val Arg
                85                  90                  95

Thr Ile Gln Asp Lys Gly Ile Val Val Gly Ile Lys Val Asp Lys Gly
                100                 105                 110

Val Val Pro Leu Ala Gly Thr Asp Gly Glu Thr Thr Thr Gln Gly Leu
                115                 120                 125

Asp Gly Leu Ser Glu Arg Cys Ala Gln Tyr Lys Lys Asp Gly Ala Asp
                130                 135                 140

Phe Ala Lys Trp Arg Cys Val Leu Lys Ile Ser Glu Arg Thr Pro Ser
```

-continued

```
            145                 150                 155                 160
Ala Leu Ala Ile Leu Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
                180                 185                 190

Pro Asp Gly Asp His Asp Leu Lys Arg Cys Gln Tyr Val Thr Glu Lys
            195                 200                 205

Val Leu Ala Ala Val Tyr Lys Ala Leu Ser Asp His His Val Tyr Leu
        210                 215                 220

Glu Gly Thr Leu Leu Lys Pro Asn Met Val Thr Pro Gly His Ala Cys
225                 230                 235                 240

Pro Ile Lys Tyr Thr Pro Glu Glu Ile Ala Met Ala Thr Val Thr Ala
                245                 250                 255

Leu Arg Arg Thr Val Pro Pro Ala Val Pro Gly Val Thr Phe Leu Ser
                260                 265                 270

Gly Gly Gln Ser Glu Glu Glu Ala Ser Phe Asn Leu Asn Ala Ile Asn
                275                 280                 285

Arg Cys Pro Leu Pro Arg Pro Trp Ala Leu Thr Phe Ser Tyr Gly Arg
        290                 295                 300

Ala Leu Gln Ala Ser Ala Leu Asn Ala Trp Arg Gly Gln Arg Asp Asn
305                 310                 315                 320

Ala Gly Ala Ala Thr Glu Glu Phe Ile Lys Arg Ala Glu Val Asn Gly
                325                 330                 335

Leu Ala Ala Gln Gly Lys Tyr Glu Gly Ser Gly Glu Asp Gly Gly Ala
                340                 345                 350

Ala Ala Gln Ser Leu Tyr Ile Ala Asn His Ala Tyr
            355                 360
```